US007931694B2

(12) United States Patent
Imran

(10) Patent No.: US 7,931,694 B2
(45) Date of Patent: *Apr. 26, 2011

(54) STOMACH PERISTALSIS DEVICE AND METHOD

(75) Inventor: Mir A. Imran, Menlo Park, CA (US)

(73) Assignee: Python Medical, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/558,473

(22) Filed: Sep. 11, 2009

(65) Prior Publication Data

US 2010/0004755 A1     Jan. 7, 2010

Related U.S. Application Data

(60) Division of application No. 11/349,309, filed on Feb. 6, 2006, now Pat. No. 7,601,178, which is a continuation of application No. 10/328,248, filed on Dec. 23, 2002, now Pat. No. 7,037,343.

(51) Int. Cl.
*A61F 2/04*     (2006.01)
*A61F 2/00*     (2006.01)
(52) U.S. Cl. ............... 623/23.65; 623/23.64; 623/23.67; 623/23.68; 600/37
(58) Field of Classification Search ............... 623/23.64, 623/23.65, 23.67, 3.1; 604/8; 600/37; *A61F 2/04*
See application file for complete search history.

(56) References Cited

U.S. PATENT DOCUMENTS

| 4,790,313 | A | 12/1988 | Borrelly |
| 4,809,676 | A | 3/1989 | Freeman |
| 5,116,494 | A | 5/1992 | Chick et al. |
| 5,261,898 | A | 11/1993 | Polin et al. |
| 5,509,888 | A | 4/1996 | Miller |
| 6,091,992 | A | 7/2000 | Bourgeois et al. |
| 6,124,523 | A | 9/2000 | Banas et al. |

(Continued)

OTHER PUBLICATIONS

International Preliminarty Examination Report of Aug. 10, 2005, International App. No. PCT/US03/41304.

(Continued)

*Primary Examiner* — David Isabella
*Assistant Examiner* — Yashita Sharma
(74) *Attorney, Agent, or Firm* — Mahamedi Paradice Kreisman LLP

(57) ABSTRACT

The invention relates to an implantable stomach prosthesis for surgically replacing or augmenting all or part of the antrum and/or pylorus of a stomach. The prosthesis controls the passage of food from the stomach to the small intestine. The prosthesis may be configured to churn ingested material and release it from the stomach through a prosthetic pyloric valve. At least one expandable member is arranged to be expanded to control the passage of food and/or to mimic the churning action of a patient's stomach. The prosthesis includes an outer support structure, a flexible inner member forming a conduit for the movement of material, and at least one expandable member located between the outer support structure and inner member. An implantable pump system is provided for inflating and deflating the expandable member(s).

3 Claims, 18 Drawing Sheets

U.S. PATENT DOCUMENTS

| | | |
|---|---|---|
| 6,395,026 B1 | 5/2002 | Aboul-Hosn et al. |
| 6,482,145 B1 | 11/2002 | Forsell |
| 6,491,623 B2 | 12/2002 | Snyder et al. |
| 6,503,189 B1 | 1/2003 | Forsell |
| 6,675,809 B2 | 1/2004 | Stack et al. |
| 6,770,024 B1 * | 8/2004 | Rastegar et al. .............. 600/16 |
| 6,953,429 B2 | 10/2005 | Forsell |
| 7,037,343 B2 | 5/2006 | Imran |
| 7,141,071 B2 | 11/2006 | Imran |
| 7,338,437 B2 | 3/2008 | Forsell |
| 7,367,938 B2 | 5/2008 | Forsell |
| 7,458,930 B2 | 12/2008 | Meretei |
| 7,530,943 B2 | 5/2009 | Lechner |
| 7,572,218 B2 | 8/2009 | Schrag |
| 7,594,885 B2 | 9/2009 | Byrum |
| 7,601,178 B2 | 10/2009 | Imran |
| 7,648,455 B2 | 1/2010 | Forsell |
| 7,775,966 B2 | 8/2010 | Dlugos et al. |
| 2001/0020189 A1 | 9/2001 | Taytor |
| 2003/0144708 A1 | 7/2003 | Starkebaum |
| 2004/0034320 A1 | 2/2004 | Burnett |
| 2004/0039452 A1 | 2/2004 | Bessler |
| 2004/0107004 A1 | 6/2004 | Levine et al. |
| 2006/0129237 A1 | 6/2006 | Imran |
| 2007/0093910 A1 | 4/2007 | Imran |

OTHER PUBLICATIONS

International Preliminarty Examination Report of Apr. 1, 2005, International App. No. PCT/US03/41305.
International Search Report of Jun. 24, 2004, International App. No. PCT/US03/41305.
International Search Report of Jun. 24, 2004, International App. No. PCT/US03/41304.
Non-Final Office Action mailed May 13, 2009 in U.S. Appl. No. 11/549,573.
Non-Final Office Action mailed Jan. 15, 2010 in U.S. Appl. No. 11/549,573.
Notice of Allowance mailed Jul. 12, 2010 in U.S. Appl. No. 11/549,573.
Written Opinion of Sep. 2, 2004, International App. No. PCT/US03/41305.
Non-Final Office Action mailed Nov. 1, 2010 in U.S. Appl. No. 11/549,573.

* cited by examiner

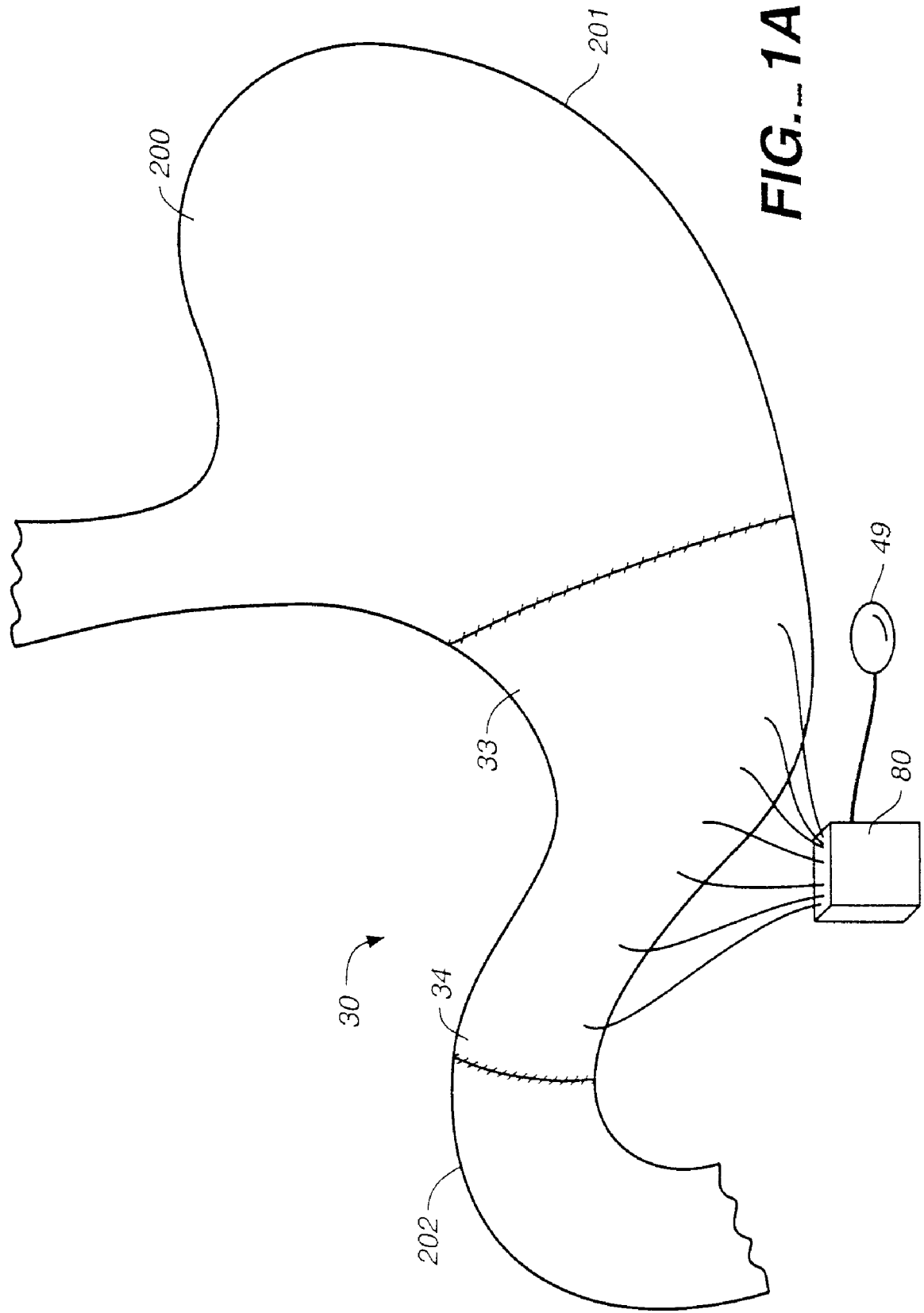
FIG._1A

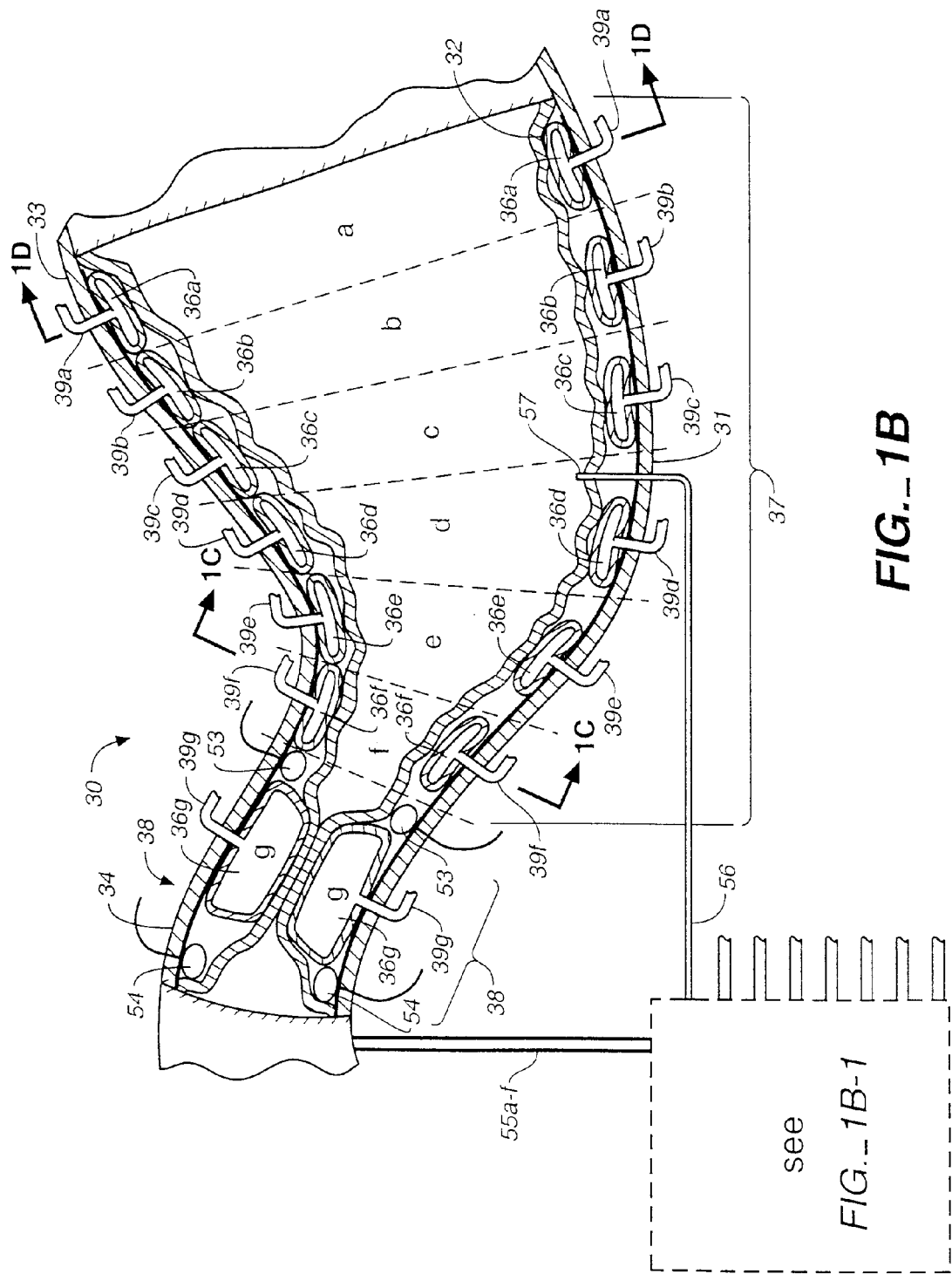
FIG._1B

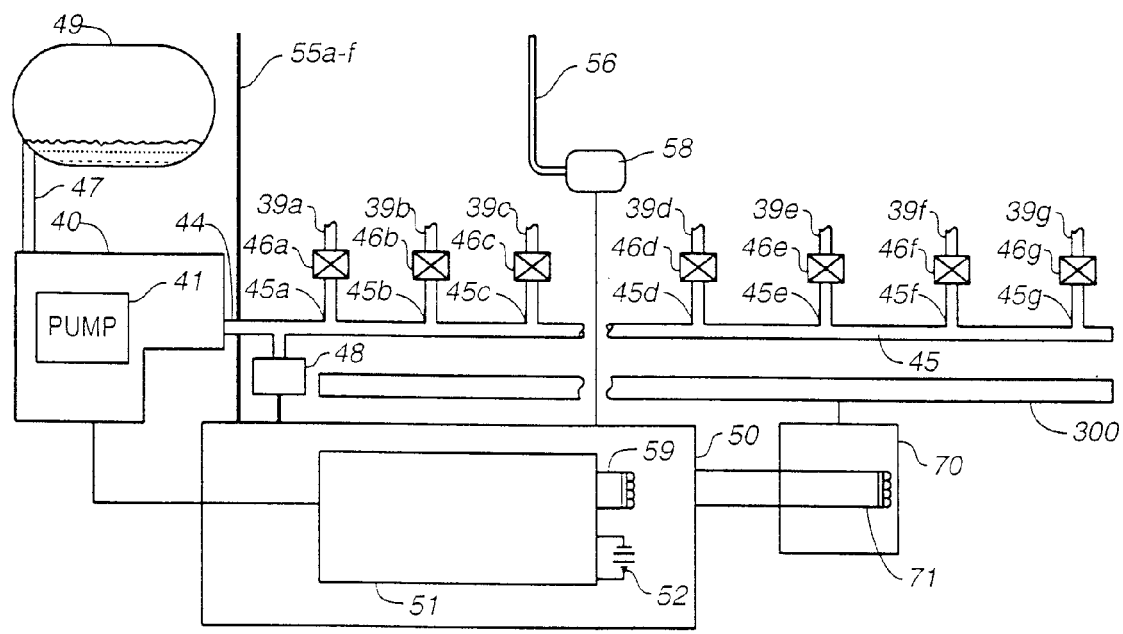
FIG._1B-1
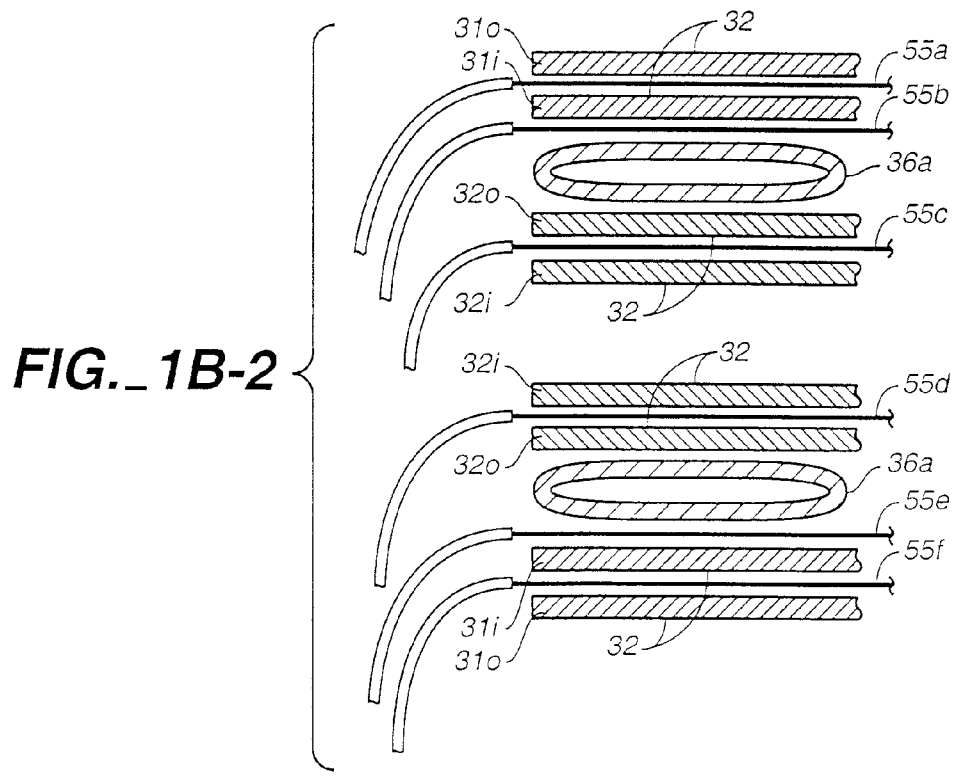
FIG._1B-2

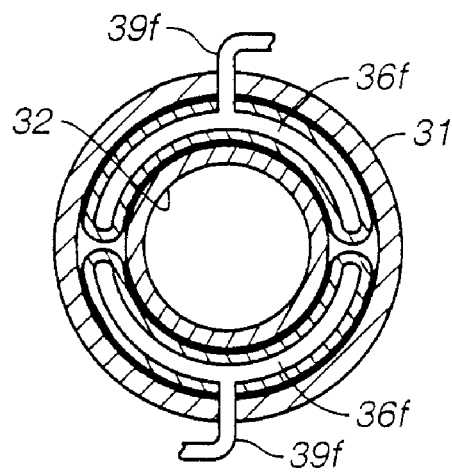
FIG._1C
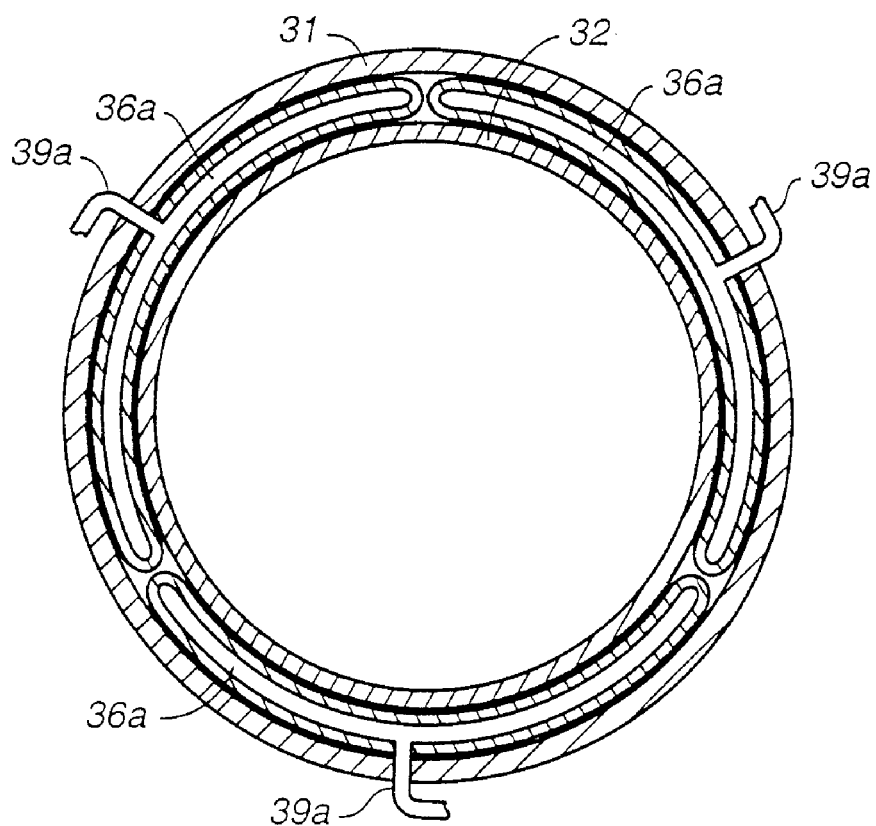
FIG._1D

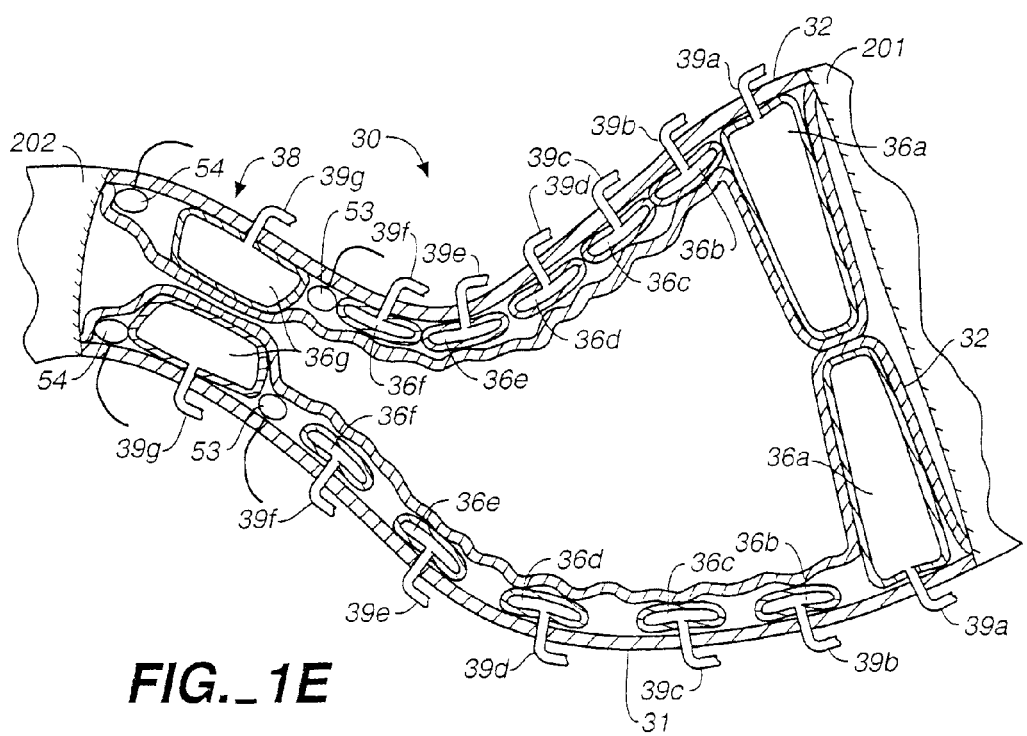
FIG._1E
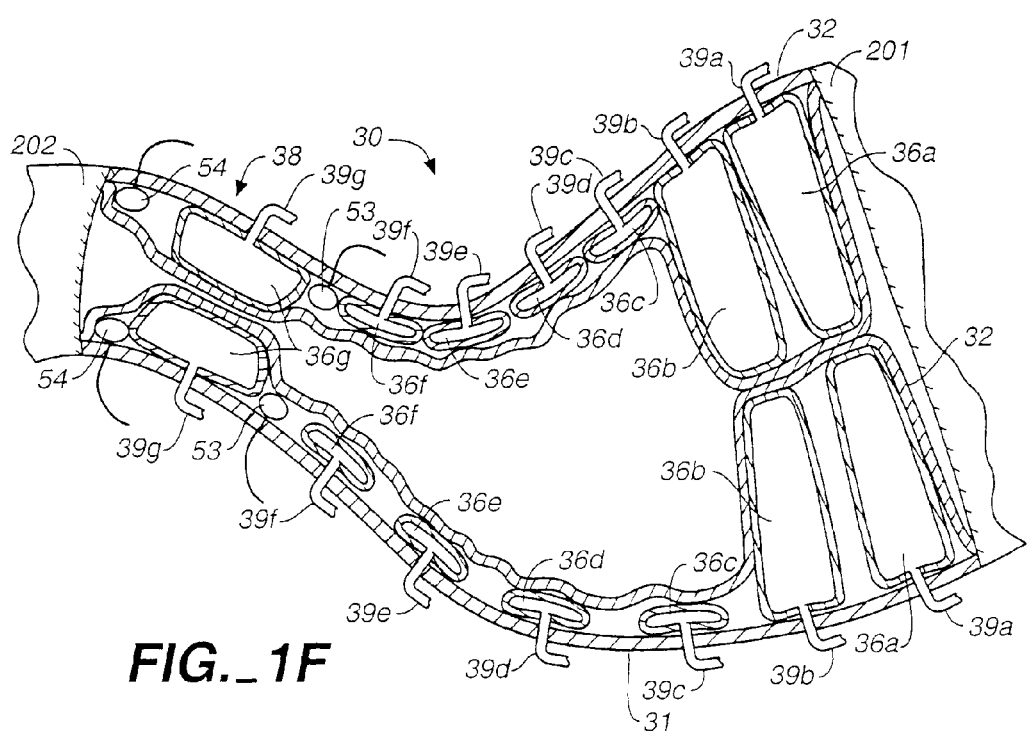
FIG._1F

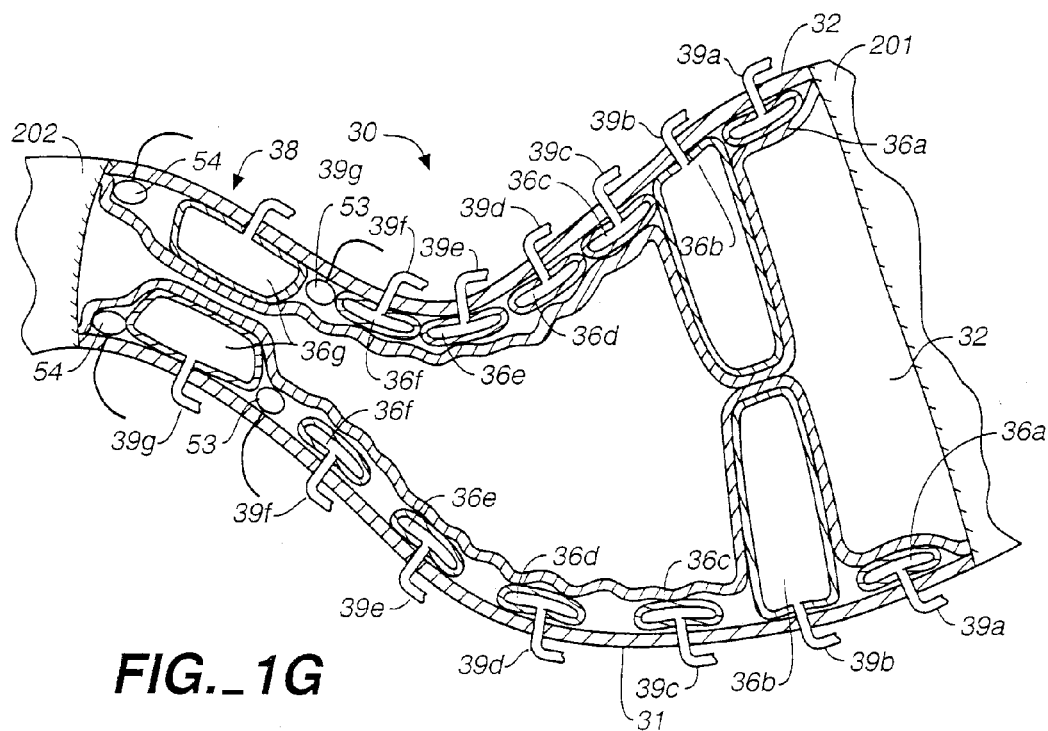
FIG._1G
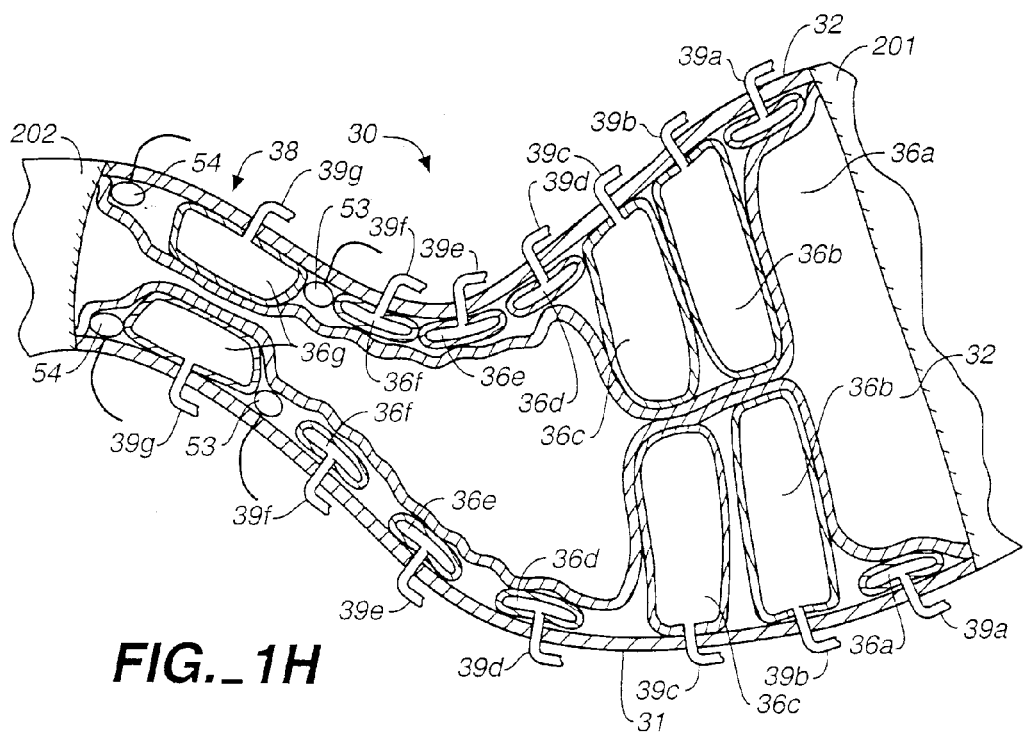
FIG._1H

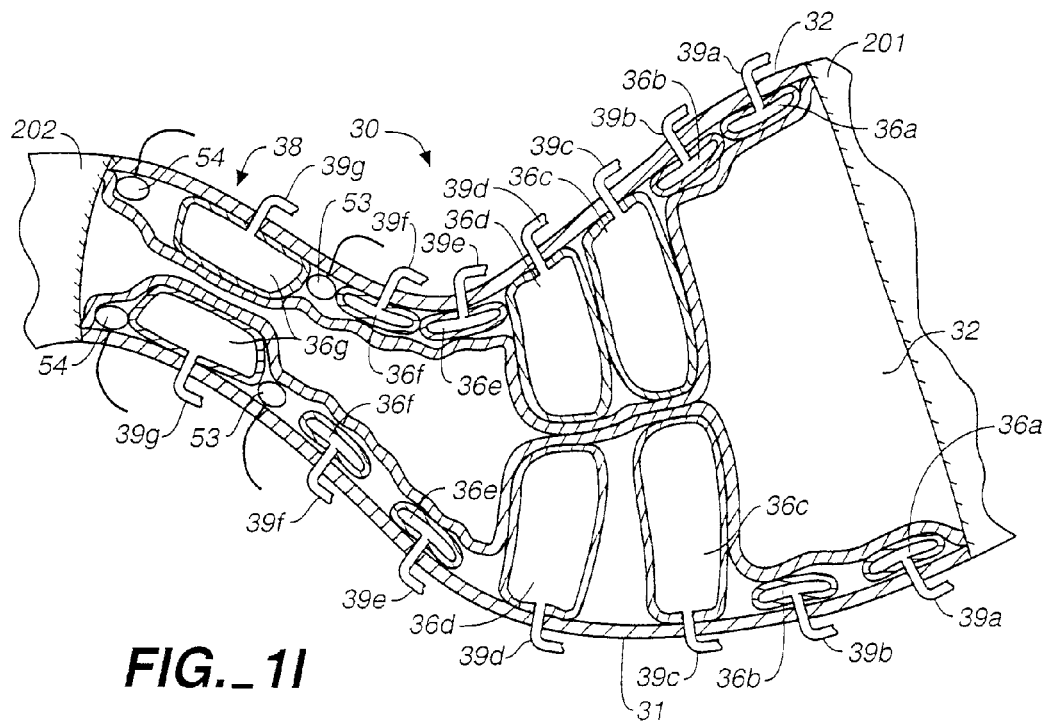
FIG._1I
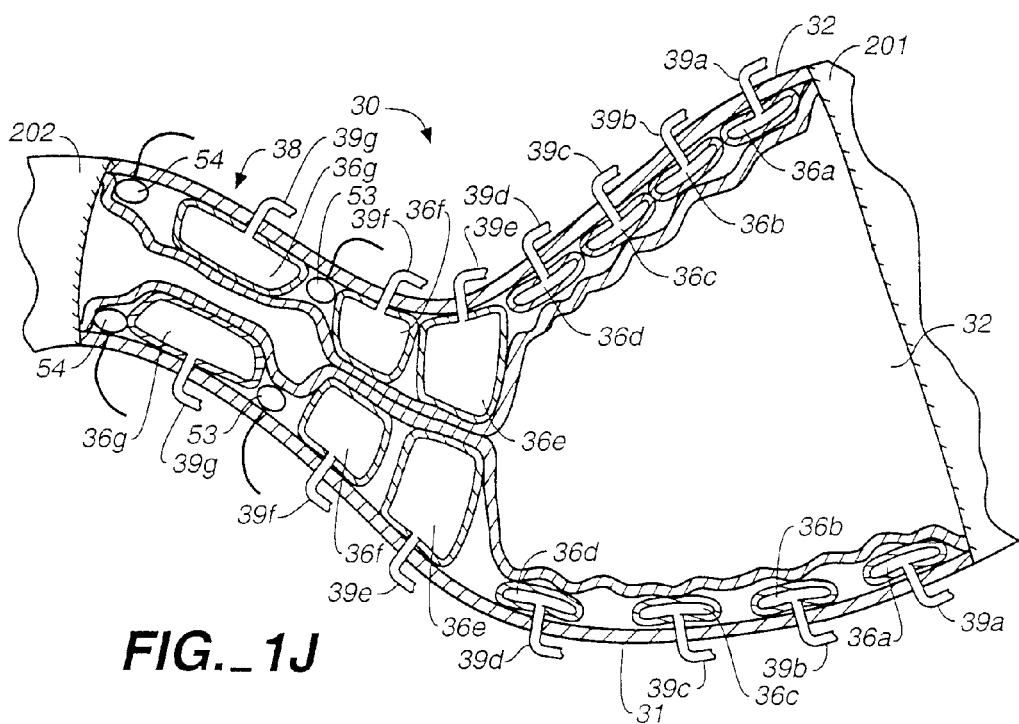
FIG._1J

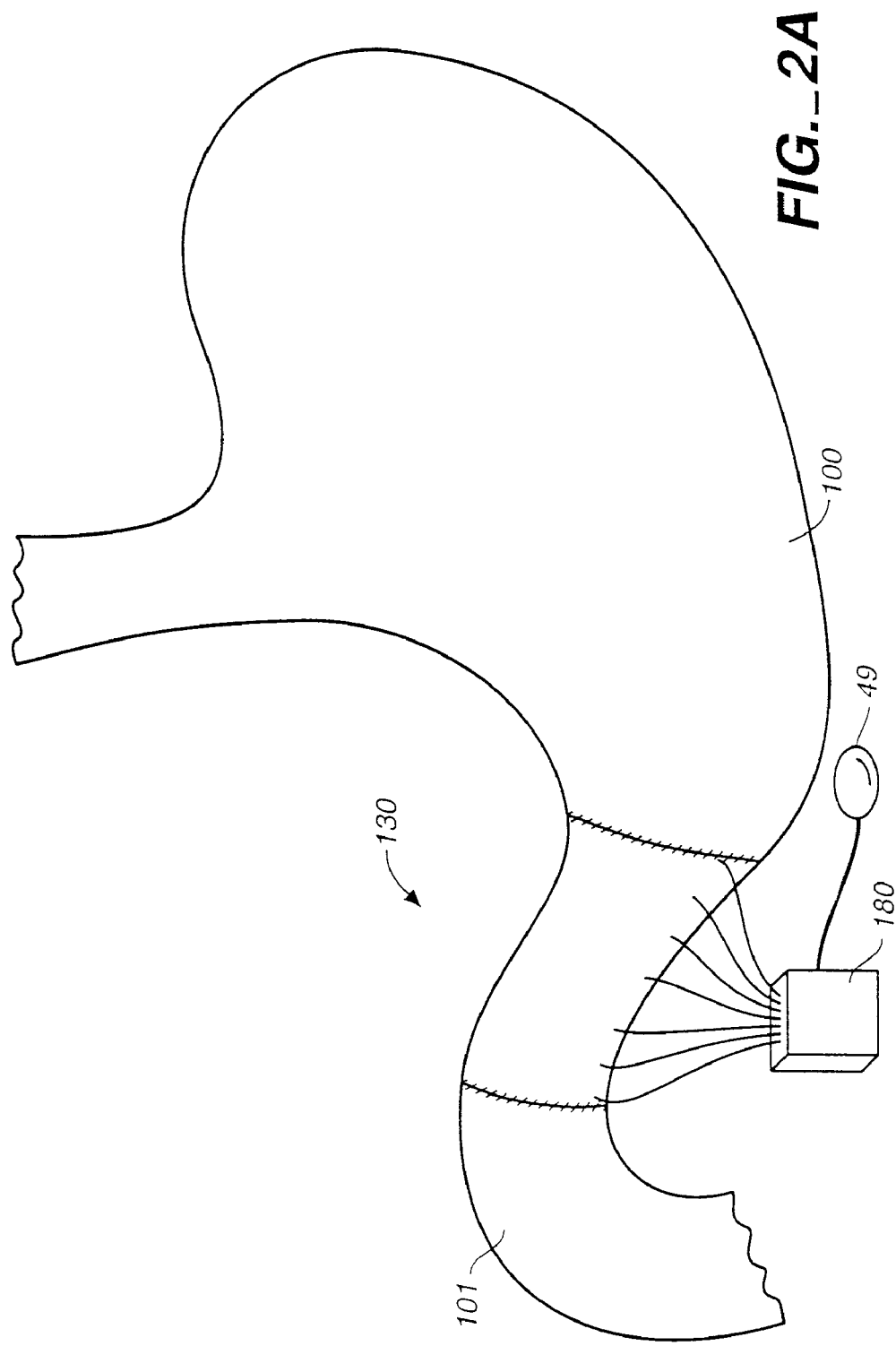

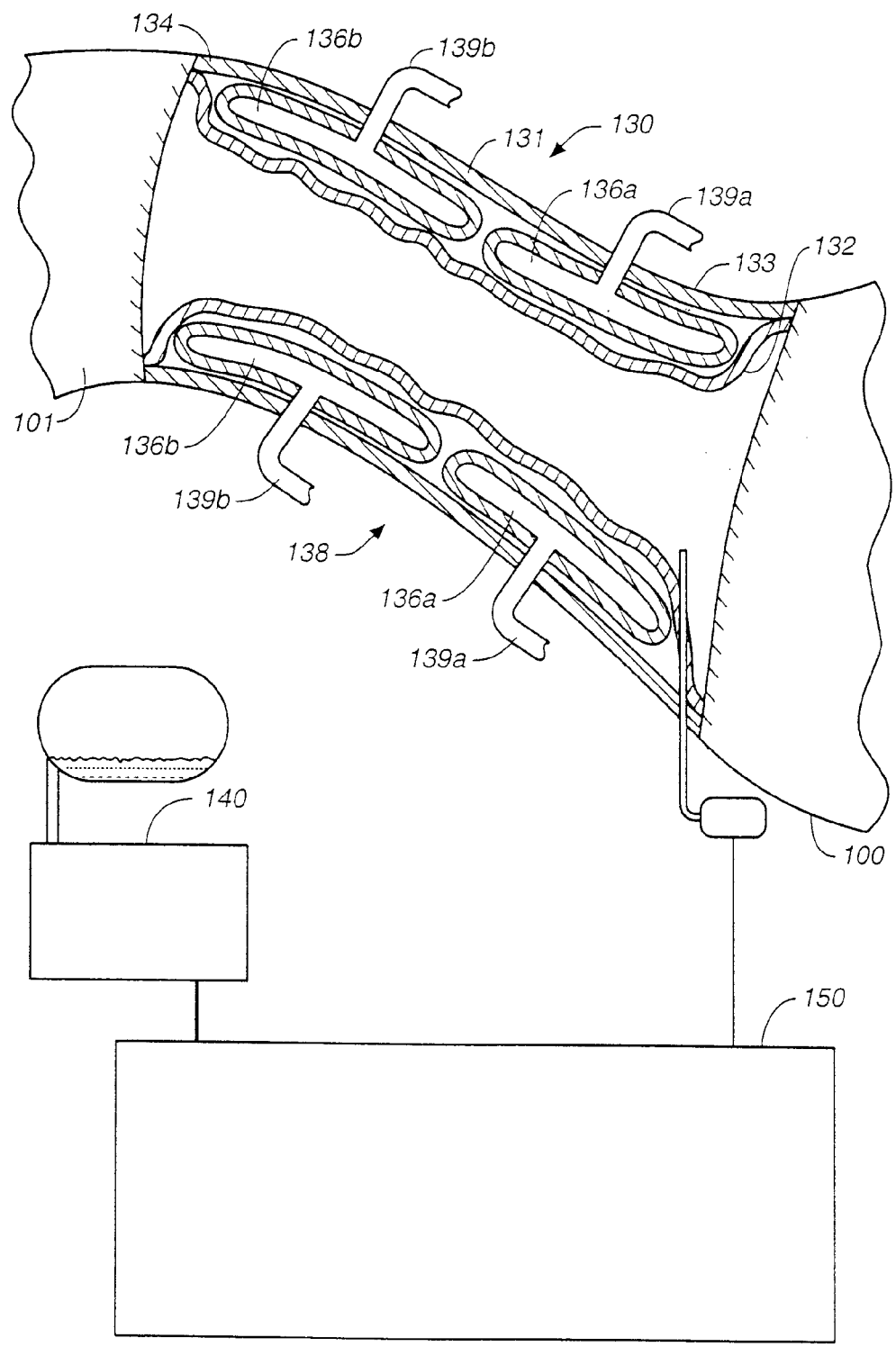
FIG._2B

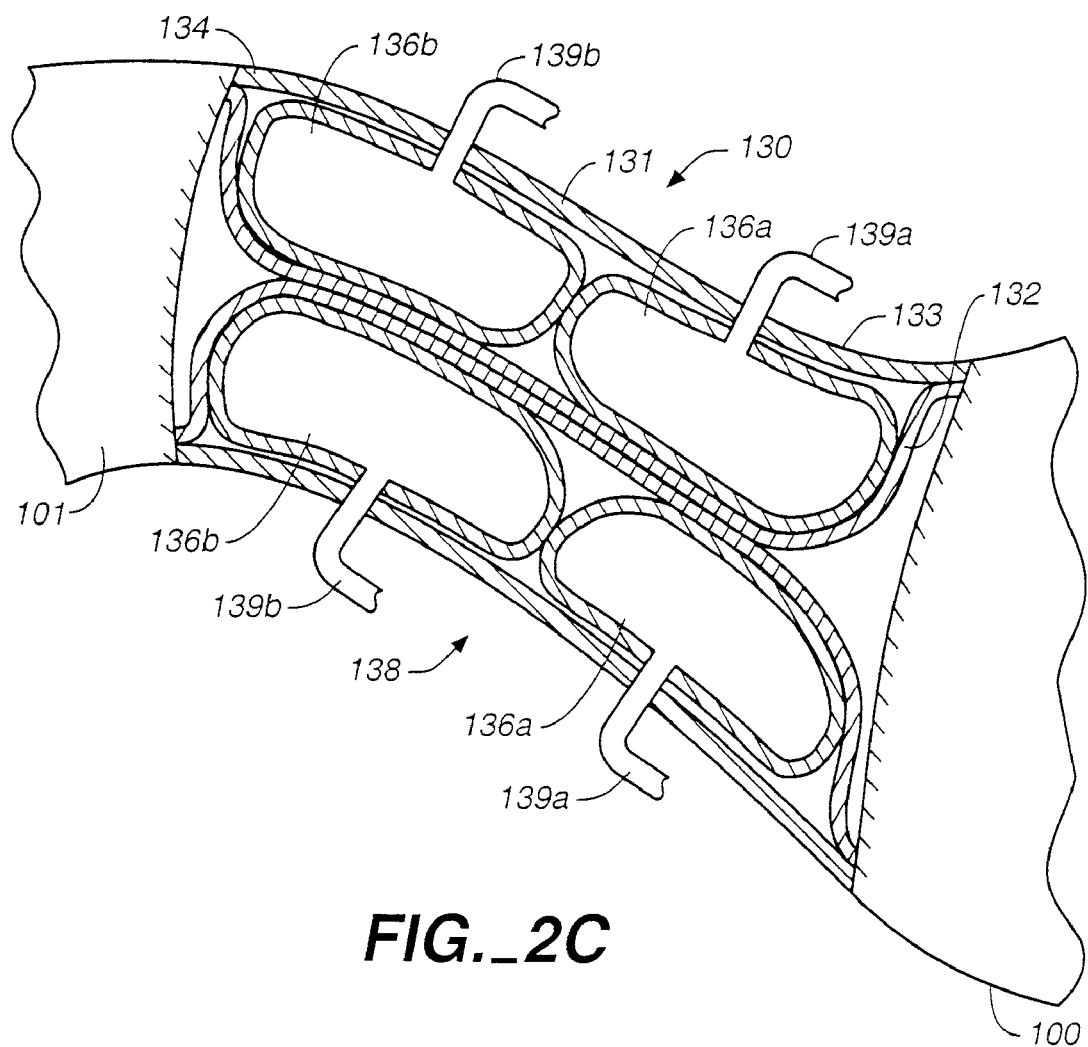
FIG._2C

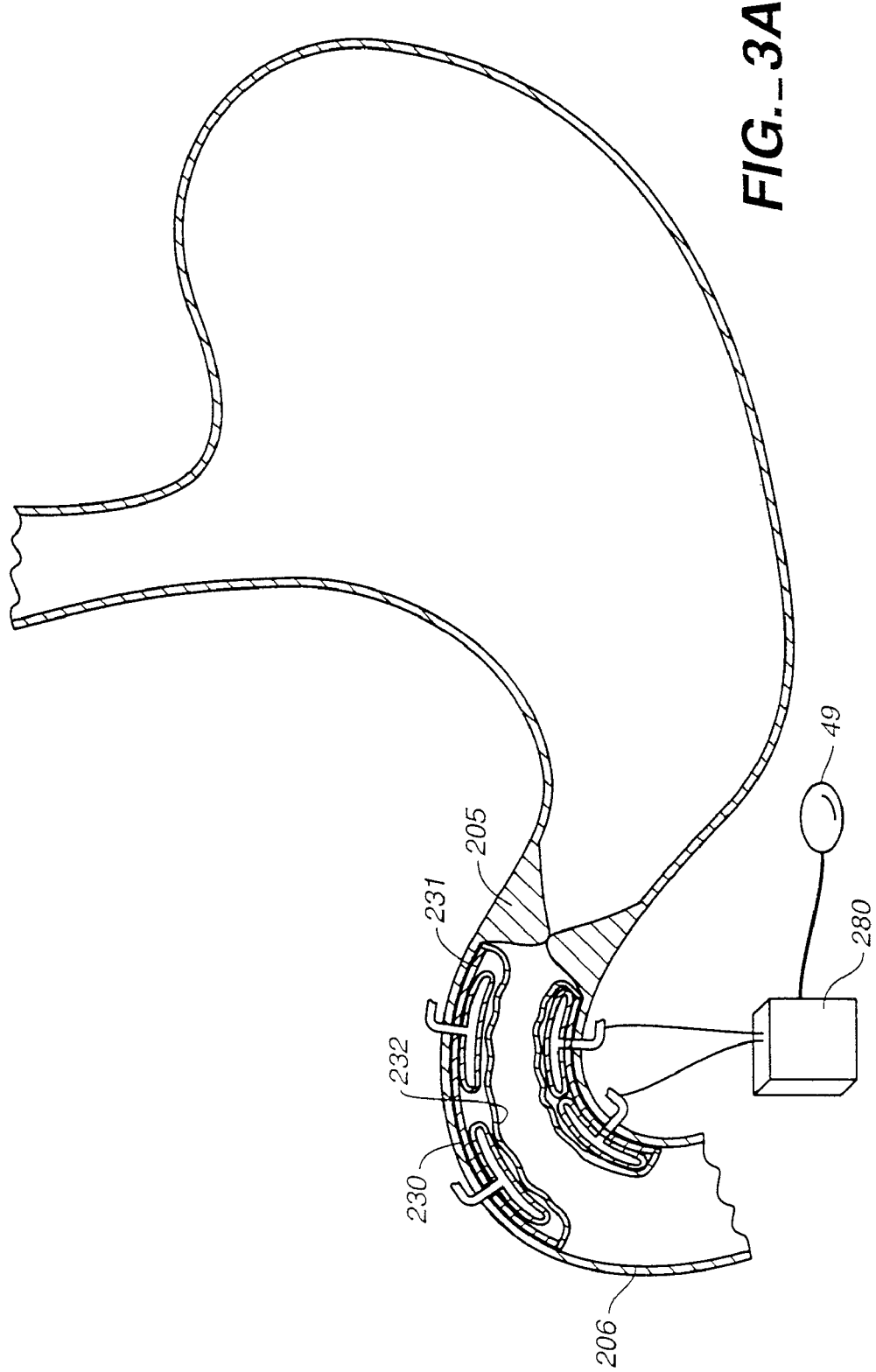

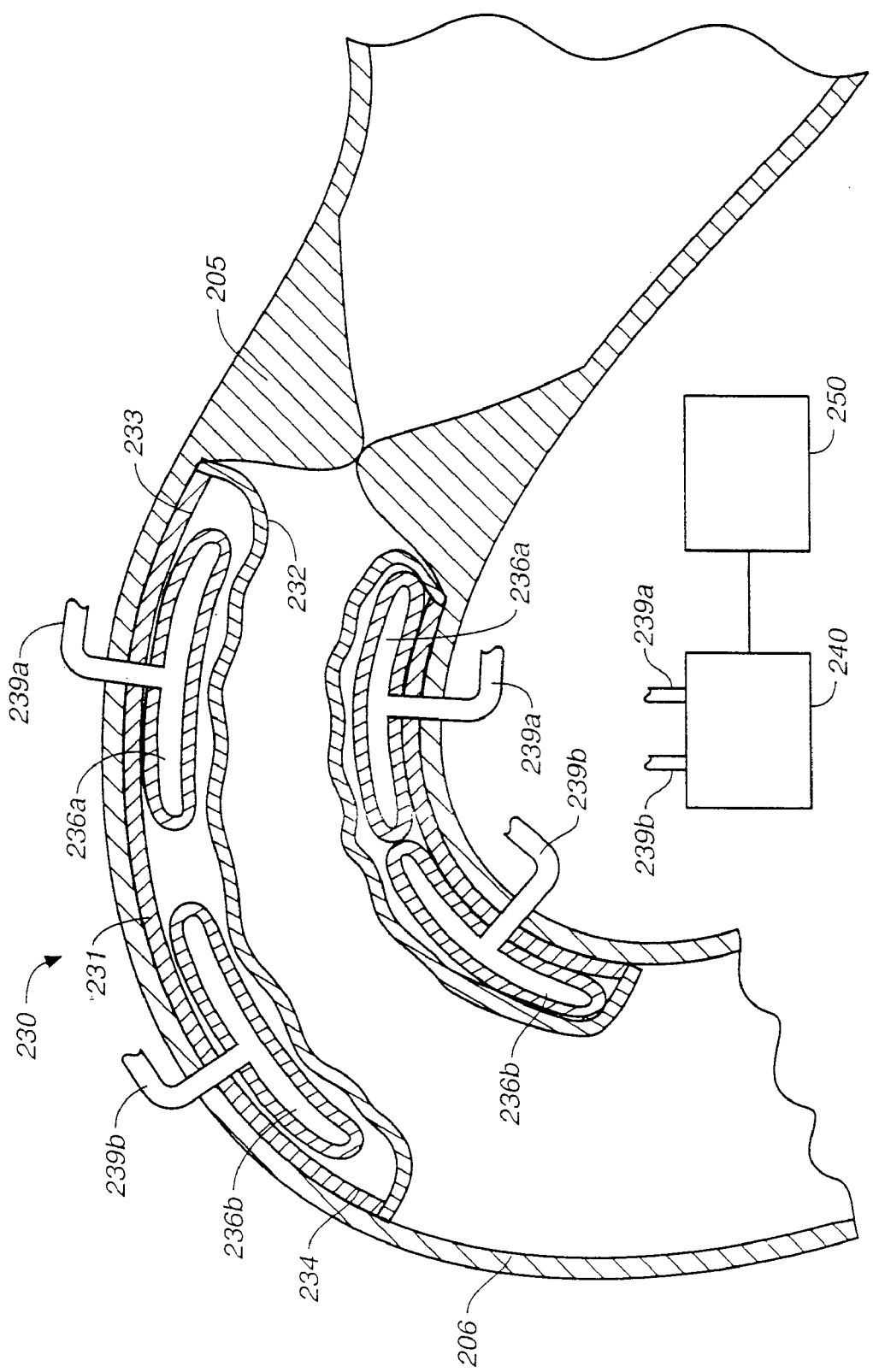

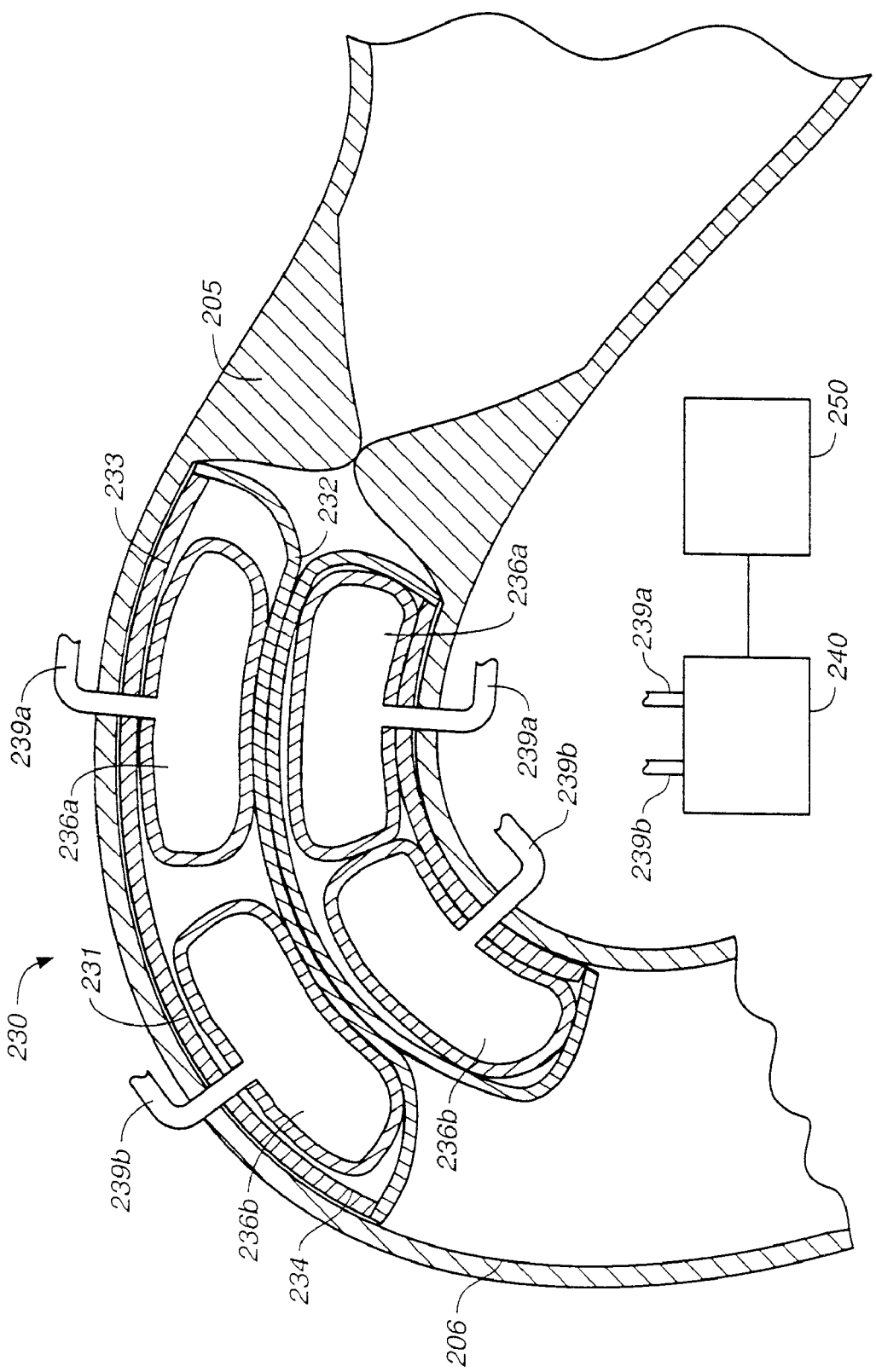
FIG._3C

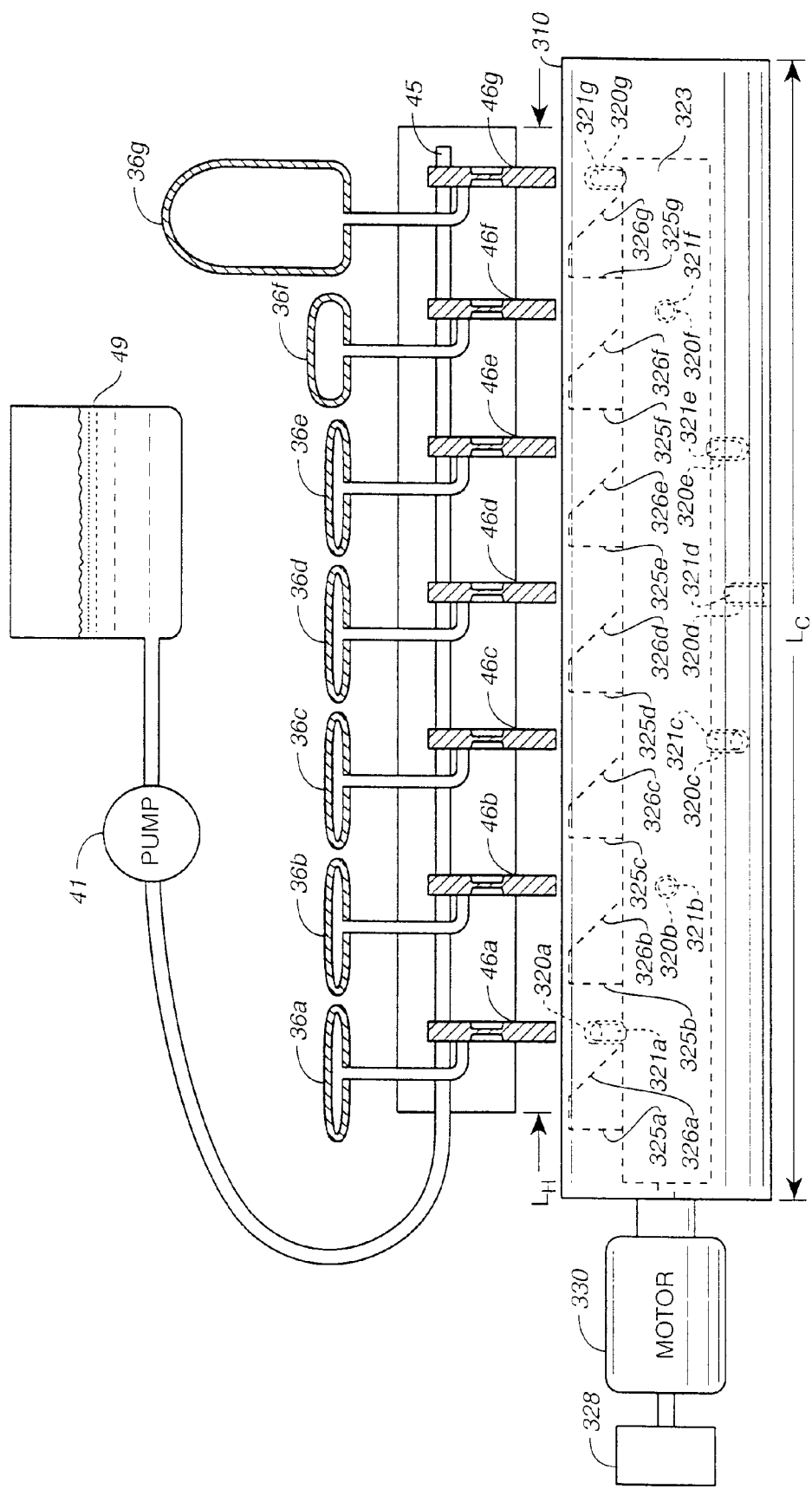
FIG._4

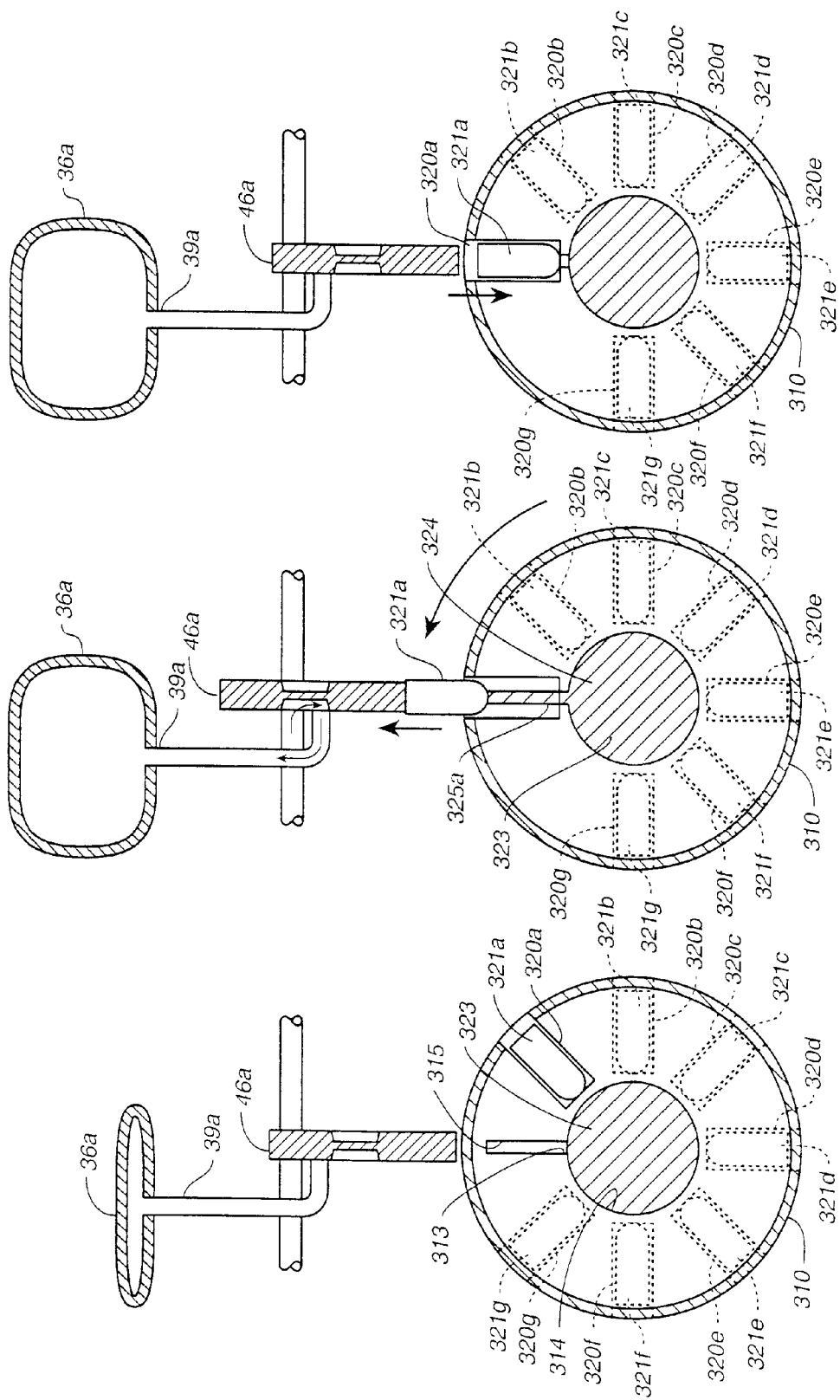

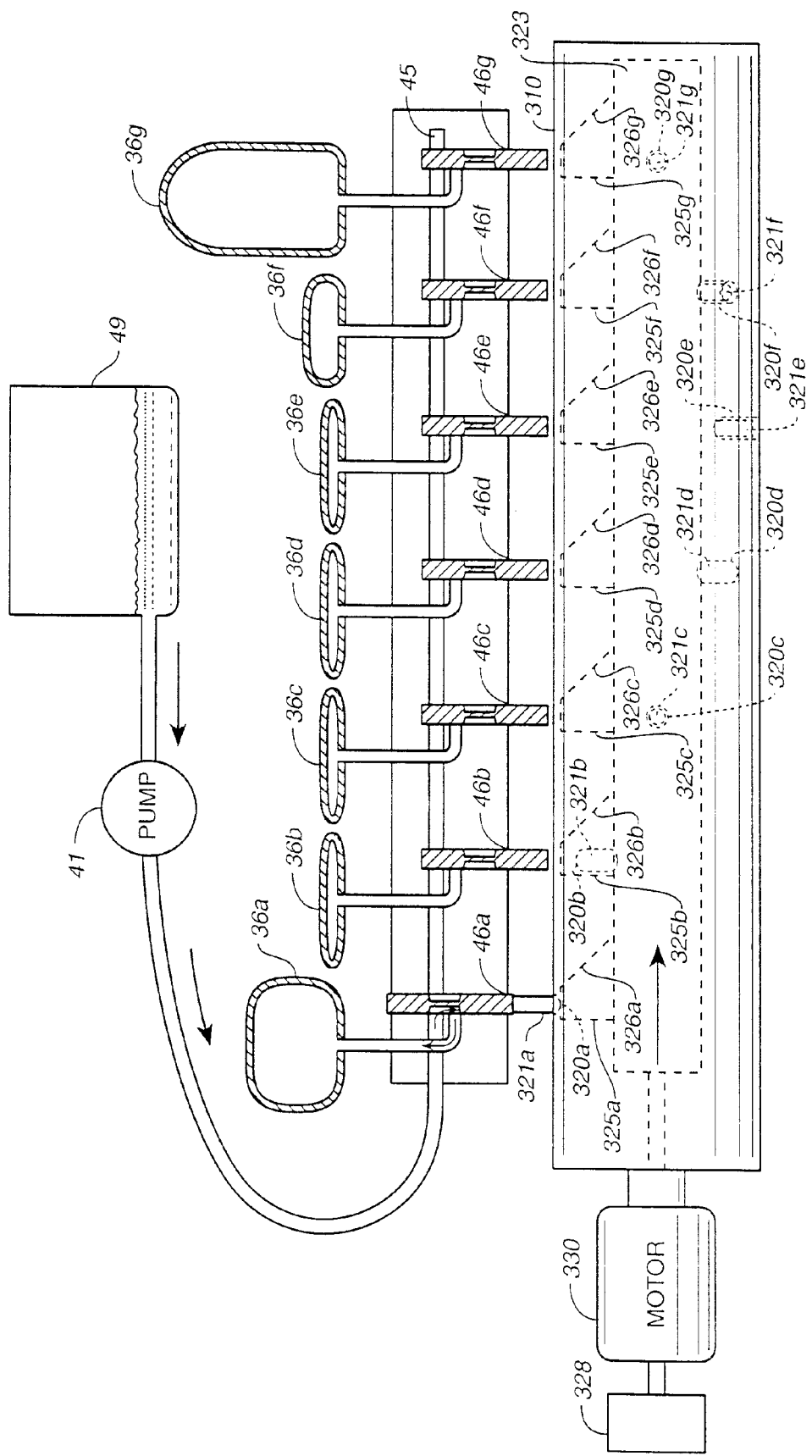

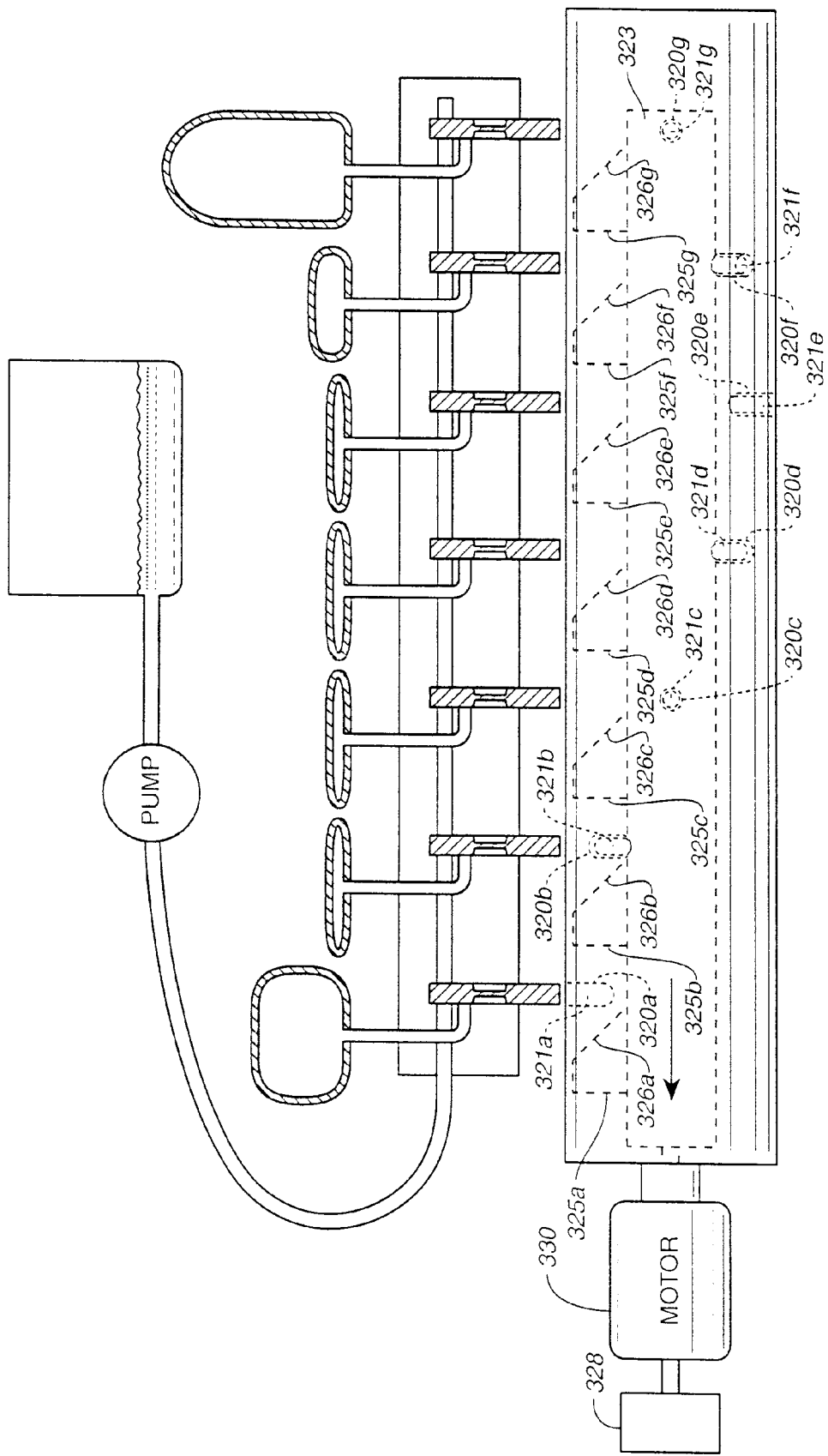
FIG._6

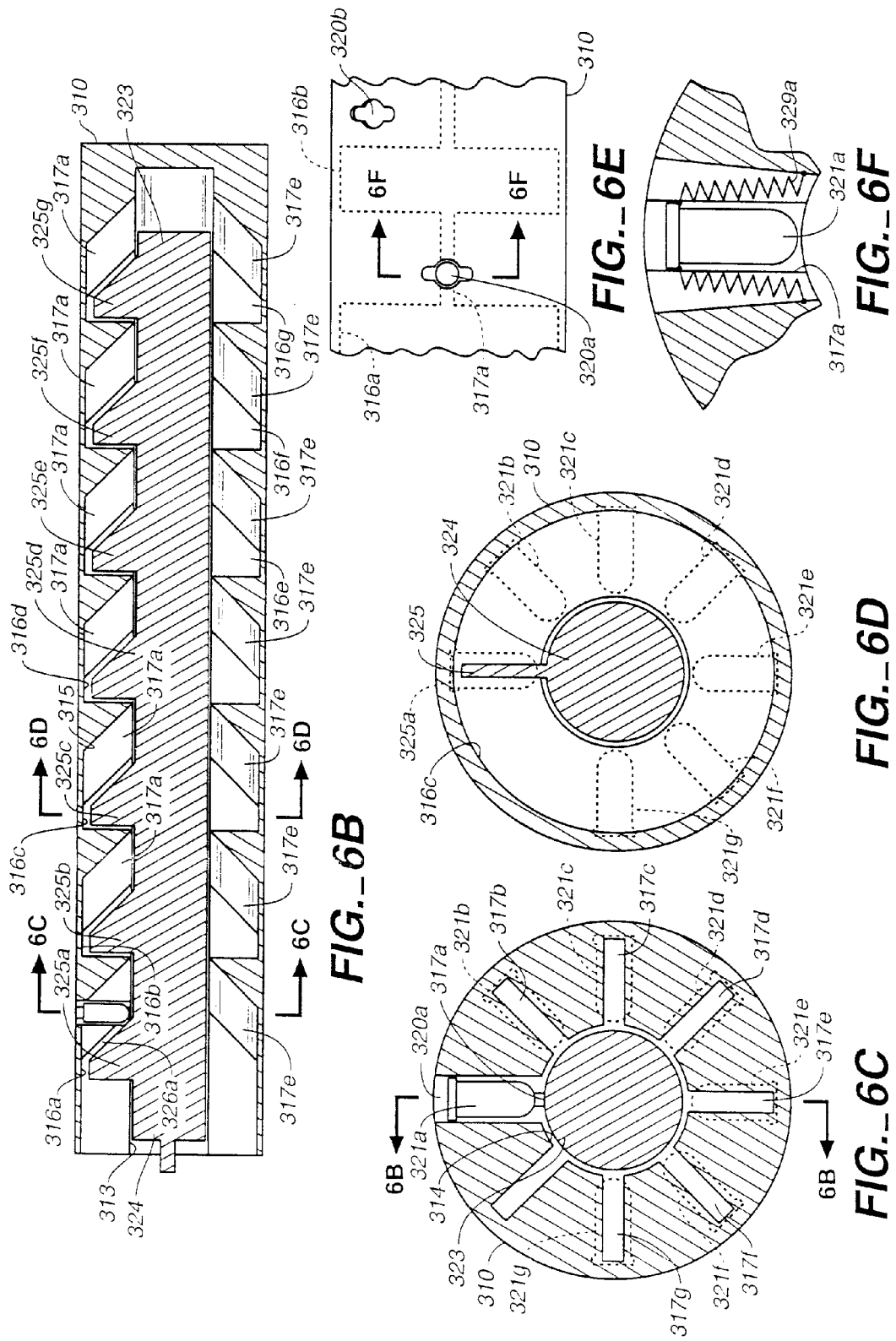

STOMACH PERISTALSIS DEVICE AND METHOD

RELATED APPLICATIONS

This application is a divisional application of U.S. patent application Ser. No. 11/349,309 filed Feb. 6, 2006, which is a continuation of U.S. patent application Ser. No. 10/328,248, filed Dec. 23, 2002, now U.S. Pat. No. 7,037,343; all of the aforementioned applications are hereby incorporated by reference in their entireties.

FIELD OF THE INVENTION

The invention relates to a stomach prosthesis for the mixing of materials in the stomach and/or the transport of materials through the stomach. In particular, the invention relates to a prosthetic stomach for replacing or augmenting a portion of the stomach, e.g., the pylorus and/or antrum.

BACKGROUND OF THE INVENTION

In general when food is ingested into the stomach, initially, the elastic upper portion or fundus accommodates the food and the fundus expands. As food enters the fundus expands there is a pressure gradient created in the stomach between the fundus and the antrum (fundus pylori). A number of things occur at this time. Fluids tend to be pushed through the pylorus, which acts as a leaky valve. Peristaltic contractions move down the stomach from the fundus into the antrum to mix and break down food and propel small particles through the pylorus into the duodenum. In healthy human stomachs, peristalsis is believed to be controlled at least in part by a region of the stomach identified near the interface of the fundus and the corpus along the greater curvature. In this region, there are cells believed to govern the organs' periodic contractile behavior of the stomach. These characteristic contractions are believed to create, a pressure gradient between the fundus pylori (or antrum) and duodenum that relates to the rate of gastric emptying. When the contractions begin, the pylorus is generally closed, although fluid and small particles leak through the valve. As contractions or electrical activity corresponding to the contractions reach pylorus, the pylorus begins to open or relax. Thus, as the stomach churns and breaks down food in a healthy stomach, the pylorus opens. As this is occurring, there may be electrically activity in the duodenum as well. Retrograde electrical activity from the duodenum, i.e., contractions or electrical activity in the direction of the pylorus tends to cause the pylorus to close, thus preventing bile and pancreatic juices from backing up into the stomach. Accordingly, the opening and closing of the pylorus is influenced by input from both of its ends.

In a number of disease states or conditions, the contractions of the stomach and/or the opening and closing of the pylorus is irregular. Gastroparesis may result in insufficient contractions to churn food, move food through the pylorus, and/or open the pylorus, among other things, resulting in gastro retention of food. In another motility disorder known as dumping syndrome, the stomach empties at an abnormally high rate into the small intestine causing various gastrointestinal disorders. It is also believed that obesity may be treated by altering gastric motility or by causing the stomach to retain food for a greater duration to slow gastric emptying.

Accordingly, it would be desirable to provide a device and method for treating motility disorders of the stomach and/or obesity.

In some disease states, portions of the stomach and/or pylorus do not function properly or may require resection. Accordingly, it would be desirable to provide a prosthetic stomach for replacing or augmenting all or part of a stomach and/or pylorus.

SUMMARY OF THE INVENTION

The present invention provides a prosthesis device and method for replacing or augmenting all or part of the pylorus or antrum of the stomach.

In one embodiment, the prosthesis is designed to facilitate or expedite mixing or breaking down of food matter or liquids in the stomach. In another embodiment, the prosthesis is designed to control, facilitate or expedite movement of food matter or liquids through the pylorus and into the small intestine. In another embodiment, the prosthesis is designed to delay passage of food from the stomach and into the small intestine.

One embodiment of the present invention provides an implantable stomach prosthesis for surgically replacing all or part of the antrum and pylorus of a stomach. The stomach prosthesis is configured to churn ingested material and release it from the stomach through a prosthetic pyloric valve. In one embodiment a plurality of expandable members are arranged to be expanded in a sequence that mimics the churning action of a patient's stomach. The stomach prosthesis includes an outer support structure to be sewn on one end to the upper portion of the stomach and an opposite end to the duodenum. The prosthesis further includes an expandable member or members located within the outer support structure, and a flexible inner member forming a conduit for the movement of material. The flexible inner member is located within the outer member and the expandable member or members are located between the inner member and the outer support structure. The expandable members are expanded and contracted, or inflated and deflated to provide a pumping action that churns and breaks down the material and pumps it through the prosthetic pylorus. The expandable members are isolated from the material moving through the prosthesis by the inner member in which all the material is contained. Thus, the material does not get caught in the interstices around the expandable members. The prosthetic pylorus, at the exit point of the stomach, is also isolated from the material by the inner member.

In one embodiment of the invention, the implantable prosthesis further comprises an implantable pump system that includes a pump and a programmable controller. According to this embodiment, the expandable members are balloons configured to receive an inflation medium to expand the expandable members. The implantable pump system includes a reservoir of sterile inflation medium used to inflate the various expandable members. The reservoir may be implantable separate from the pump, e.g. in soft tissue. In general, the pump system is a closed system where the inflation medium is stored or transported as it is pumped from one inflation member to another. The prosthesis may be divided along its length into sections. A section may include a single expandable member or a plurality of expandable members that may be separately inflated or may share a conduit coupled to a single output port and valve on the pump. Preferably, each of the expandable members or sections of expandable members has an input port and valve coupled to the pump such that only one valve is opened at a time. However, the system may alternatively have more than one valve open at a time.

The controller controls the inflation and deflation of the expandable members by controlling the opening and closing of the valves coupled to each of the expandable members, and by controlling the pump direction and pressurization of the expandable members. In one embodiment, the inflatable members are inflated to a predetermined pressure. The pump may determine the inflation pressure by monitoring the pumping action or work of its motor. The inflation pressure may also be sensed by sensors that sense the pressure of the system, e.g. in the fluid header of the pump system. According to one embodiment, in a first churning mode, a first section of expandable members corresponding to a first section of the antrum is inflated, then a second adjacent section is inflated. The second section is inflated before the first section is deflated so that the material in the prosthesis cannot move back in an orad direction when the second section is inflated a number of subsequent inflation member sections may then be inflated and deflated in a manner that mimics the stomach's mixing and churning of food material. In this mode, the prosthetic pyloric valve may be partially open to permit liquid and small particles to pass through the pylorus into the small intestine.

A second mode may be employed to empty the stomach. According to one embodiment of this second mode, a first section of expandable members corresponding to a first section of the antrum is inflated, then a second adjacent section is inflated. The second section is inflated before the first section is deflated so that the material in the prosthesis cannot move back in an orad direction when the second section is inflated. The first section is then deflated. Then the third section is inflated, etc. until the section adjacent the pylorus is inflated. According to this mode the pylorus may be opened further to permit passage of more food material. If the food has not been sufficiently broken down to pass through the pylorus, the churning mode may be repeated.

In either of these modes sensors may be employed on each side of the pyloric valve to sense pressure or changes in pressure. The pyloric valve may be relaxed or tightened depending on the sensed pressure. For example, if there is an increased pressure from the duodenum side of the pyloric valve, the pyloric valve is tightened to prevent back flow of material, e.g., bile, from the small intestine. If there is an increased pressure from the stomach side of the pyloric valve, the valve may be relaxed to permit movement of material from the stomach into the small intestine.

The controller may also control selection of a section of the stomach organ for the churning or breaking down of material. The controller may control selection of sections of the organ for peristaltic movement or moving material through the stomach organ. Accordingly, sections may be selected according to a desired sequence of the section actuation. The controller may be preprogrammed to control the peristalsis pattern or may be reprogrammed externally or in response to sensed conditions at various locations in the prosthesis. For example the sensors may sense presence or absence of material in the prosthesis and may direct a pattern of peristaltic movement in the various sections accordingly.

In one embodiment, a single electromechanical device actuates the opening and closing of the valves according to the sequence. The valve actuator selectively actuates a particular valve at a given time according to instructions from the controller.

The pump and the valve actuating mechanism may be powered through a coil inductively coupled transcutaneously to an external power source, or by a battery rechargeable through such coil and external power source. According to one embodiment, a user positions and actuates the external power source to actuate the prosthesis. The electronics unit may be powered by a rechargeable or replaceable battery as the controller consumes relatively little power in its operation.

In another embodiment, the prosthesis is a prosthetic pyloric valve. According to this embodiment, a pyloric valve is replaced with a prosthesis comprising an outer member, an inner member and one or more sections of inflatable members between the outer and inner member. The inflatable member sections are selectively inflated and deflated to control the opening and closing of the pylorus. The prosthesis may include pressure sensors on opposite ends of the valve. The pressure sensors sense pressure in the stomach and duodenum and the opening and closing of the valve is adjusted accordingly. For example, a pressure increase from the duodenum would trigger the closure of the valve to prevent backflow of material into the stomach. An increasing pressure from the stomach may trigger a relaxing of the valve to permit materials to pass out of the stomach.

In another embodiment, the natural pyloric valve is augmented by implanting a pyloric prosthesis in the duodenum adjacent the pyloric valve. In this embodiment, the prosthesis may act to prevent material from passing into the small intestine even when the natural pyloric valve is open. Thus the augmented prosthetic pylorus may be used to retain food in the stomach for a greater length of time, e.g., to prevent gastric dumping or to treat obesity. According to this embodiment, one or more inflatable members sections are provided between an inner member and an outer member. The outer member is sutured onto the inside of the duodenum intestinal wall, just below the pylorus. Inflation conduits extend from the expandable member out of the outer support member and intestine. The conduits are coupled to an implanted pump that inflates and deflates the inflation member sections as desired to retain or pass food.

BRIEF DESCRIPTION OF THE DRAWINGS

FIG. 1A is a side view of a prosthetic stomach device attached to a stomach according to an embodiment of the invention.

FIGS. 1B and 1B-1 are schematic side views of the prosthesis of FIG. 1A in a relaxed position, including a pump, valve actuating device and controller.

FIG. 1B-2 is an enlarged view of a portion of the prosthetic stomach of FIG. 1B illustrating the wire sensors.

FIG. 1C is a cross-section of FIG. 1B along the lines 1C-1C.

FIG. 1D is a cross-section FIG. 1B along the lines 1D-1D.

FIG. 1E is a schematic side view of the prosthesis of FIG. 1A a first actuated position.

FIG. 1F is a schematic side view of the prosthesis of FIG. 1A in another actuated position.

FIG. 1G is a schematic side view of the prosthesis of FIG. 1A in another actuated position.

FIG. 1H is a schematic side view of the prosthesis of FIG. 1A in another actuated position.

FIG. 1I is a schematic side view of the prosthesis of FIG. 1A in another actuated position.

FIG. 1J is a schematic side view of the prosthesis of FIG. 1A in another actuated position.

FIG. 2A is a side view of a prosthetic stomach device attached to a stomach according to an embodiment of the invention.

FIG. 2B is a schematic side view of the prosthesis of FIG. 2A in a relaxed position.

FIG. 2C is a schematic side view of the prosthesis of FIG. 2A in a closed position.

FIG. 3A is a schematic side view of a prosthetic stomach device attached to a stomach according to another embodiment of the invention.

FIG. 3B is a schematic side view of the prosthesis of FIG. 3A in a relaxed position.

FIG. 3C is a schematic side view of the prosthesis of FIG. 3A in a closed position.

FIG. 4 is a schematic of a miniature valve-actuating device for controlling the valves of the pump of an embodiment of the invention in a first position with a valve closed and a rotational position in which none of the openings of the device are aligned with a valve.

FIG. 4A is an end view of the device as illustrated in FIG. 4 in the first position.

FIG. 5 is a schematic of the valve-actuating device of FIG. 4 in a second position.

FIG. 5A is an end view of the device illustrated in FIG. 5 with the valve open and an inflation being inflated.

FIG. 6 is a schematic of the micro valve-actuating device in the rotational position of FIG. 5 with the valve closed and the inflation member in an inflated position.

FIG. 6A is an end view of the device illustrated in FIG. 6.

FIG. 6B is a schematic side cross-section of the cylinder and rod of FIG. 6.

FIG. 6C is a cross section of FIG. 6B along the lines 6B-6B.

FIG. 6D is a cross section of FIG. 6B along the lines 6D-6D.

FIG. 6E is a top view of the cylinder of FIG. 6.

FIG. 6F is a cross section of a portion of the cylinder as illustrate in FIG. 6E along the lines 6F-6F.

DETAILED DESCRIPTION OF THE INVENTION

Referring to FIG. 1A, a prosthetic stomach 30 is illustrated attached to the upper portion 201 of the stomach 200 at the orad end portion 33 of the prosthetic stomach 30 and to the duodenum 202 at the aborad end portion 34 of the prosthetic stomach 30. An implantable pump system 40 (FIG. 1B-1) and electronics unit 50 (FIG. 1B-1) are contained in a housing 80 coupled to the prosthetic stomach 30. The pump system 40 and electronics unit control the inflation and deflation of inflatable members 36a-g (FIG. 1B) that are inflated and deflated according to a desired protocol, to actuate the stomach prosthesis 30. A bladder 49 of the pump system 40 is located externally of the housing, within the patient's soft tissue.

A schematic of the prosthesis of one embodiment is illustrated in FIGS. 1A-1J. The prosthesis includes a prosthetic stomach 30, a hermetically sealed pump system 40 and a hermetically sealed electronics unit 50 including a controller 51 for controlling the pump system 40. The pump system 40 and electronics unit 50 may be contained in the same housing 80 illustrated in FIG. 1A or may alternatively be separate.

The prosthetic stomach 30 includes an outer support member 31, a series of inflatable member sections 36a-g, and an inner member 32. The inflatable member sections 36a-g each comprise a plurality of opposing inflatable members that when inflated act to close together and squeeze the inner member 32. Each inflation member section 36a-f corresponds to a particular section a-f of the prosthetic stomach 30. In this particular embodiment, inflatable member sections 36a-d each comprise three inflatable members where the prosthetic stomach 30 is larger (See FIG. 1C), and inflatable member sections 36e-g each comprise two inflatable members where the prosthetic stomach 30 is narrow (See FIG. 1D).

The outer support member 31 comprises a flexible, relatively inelastic material such as, for example, polyethylene or polyurethane, and provides structural support for the prosthetic stomach 30 (alternatively an elastic material may be used). The prosthesis sections a-f and inflatable member sections 36a-f form an antrum portion 37 of the stomach. Section g and inflatable member section 36g form a prosthetic pyloric valve 38 at the aborad end portion 34 of the stomach prosthesis 30. The inner member 32 comprises a thin-walled, non-elastic flexible material such as polyethylene or polyurethane. The inside of the inner member 32 may be coated with an antibiotic surface, such as a silver coating, to reduce bacterial growth. The inner member 32 is attached to the outer support member 31 at the orad end portion 33 and the aborad end portion 34 of the prosthetic stomach 30 (for example, by welding) to provide an isolated cavity where material is mixed, broken down and passed through the pyloric valve 38. The orad end portion 33 of the outer support member 31 includes an extended portion for suturing the outer support member 31 to the upper portion of the stomach 201. The inflatable member sections 36a-g are located between the outer support member 31 and the inner member 32. The inner member 32 floats relatively loosely within the outer support member 31 so as to permit movement including the inflation and deflation of the inflatable member sections 36a-g.

Although sections 36a-g are illustrated, the number of inflation member sections depend on a selected prosthesis size, the size of the patient or the amount of the stomach to be replaced.

Each of the inflation members of a section converge together when inflated, to churn or move material in the prosthetic stomach 30. Each inflatable member section 36a-g is coupled to and is in fluid communication with a corresponding one of conduits 39a-g, respectively. Conduits 39a-g are used to selectively deliver inflation medium to and from inflatable members 36a-g by an implanted pump system 40.

As illustrated in FIG. 1B, a controller 51 of an electronics unit 50 controls the implantable pump system 40 to selectively inflate and deflate inflatable member sections 36a-g. The pump system 40 includes a bi-directional hydraulic pump 41 having an intake 47 coupled to a fluid reservoir 49 and an output 44 in fluid communication with a header 45 having fluid ports 45a-g. The bi-directional pump 41 may be configured in a number of ways to provide pumping in two directions, for example, by controlling a series of valves that direct fluid into or out of the reservoir 49 or by providing a DC powered reversible pump. The fluid reservoir 49 contains a sterile, radiopaque inflation medium sufficient to inflate two sections of inflation members 36a-g or a combination thereof at a given time. The fluid reservoir 49 may be implanted at a location adjacent to or away from the pump system 40 (e.g. in soft tissue) or alternatively may be included with the pump system.

Each fluid port 45a-g is coupled to a respective valve 46a-g, which is coupled to a respective conduit 39a-g. Each conduit 39a-g is coupled to a corresponding inflation member pair 36a-g. The valves 46a-g are controlled by a valve actuating device 300 which operation is controlled by the controller 51 of the electronics unit 50. The valves 46a-g in this particular embodiment are controlled by a electromechanical device described in more detail with reference to FIGS. 4-6F. Alternative valve actuating mechanisms are also contemplated, for example, individually operated bistable solenoid valves may be used.

A pressure transducer 48 is located between the output 44 of the pump 41 and the header 45. The pressure transducer 48 senses the pressure of the fluid of a particular section of inflation members when the corresponding solenoid valve of the corresponding port is in an open position. The pressure transducer 48 is coupled to the controller 51, which controls the pump 41 in response to a sensed pressure.

Sensors 53 and 54 are located on opposing ends of the inflation member section 36g (forming the pyloric valve 38) between the outer support member 31 and the inner member 32. Sensor 54 is located on the antrum side while sensor 54 is location on the duodenum side. The sensors 53, 54 are coupled to the electronics unit 50 by leads. The sensors 53, 54 are used to sense pressure on either side of the valve 38. When the pressure increases or reaches a threshold level on the stomach side of the valve 38, the pyloric valve is relaxed by partially deflating the inflation member section 36g. When the pressure increases or reaches a threshold level on the duodenum side of the valve 38, the valve 38 is tightened to prevent backflow into the stomach. The pressure sensors 53, 54 are coupled to a controller which can compare the pressures sensed by each of the sensors 53, 54 and provide a control signal that will control the resulting desired inflation or deflation of the valve 38 based on the sensed pressures or pressure differentials. The relative pressure on each side of the valve 38 as compared to the other side of the valve 38 may be used to control the valve 38 as well.

The electronics unit 50 includes a controller 51 and a battery 52 powering the controller 51. The controller 51 is programmed to control the action of the various elements of the prosthesis and to respond to various sensed conditions. The controller 51 is coupled to the pump system 40 and controls when and in which direction the pump 41 is actuated. The controller 51 is also coupled to a valve-actuating device 300 that opens and closes the valves 46a-g according to a program stored in the controller 51, thereby sequentially inflating and deflating inflation member sections 36a-g. According to one embodiment, only one valve is open at a time. The controller 51 also includes a telemetry coil 59 for communicating information to and receiving information from an external device. The external device may be used to program operation parameters into the controller 51. The external device may also receive signals from the controller 51 or electronics unit 50 representative of various sensed conditions, e.g., pressure or system leaks. The external device may program or reprogram the controller 51 based on sensed parameters or other patient conditions. An external device may also power the pump 41 and the valve-actuating device 300 through an electronics unit 70 comprising an electromagnetic coil 71 for inductively receiving power from an external source. The electromagnetic coil 71 is coupled to the electronics unit 50, which includes a voltage regulating circuit. The electronics unit 50 and controller 51 control the pump 41 by powering the pump and controlling the valve actuating device 300. The voltage regulating circuit of the electronics unit 50 operates to convert a high frequency AC signal to a regulated voltage signal that powers the pump 41 and valve actuating mechanism 300. Alternatively, coil 59 may be used for both powering the pump and electronics unit 50 and for bi-directional telemetry communication.

The prosthetic stomach 30 also further includes wires 55a-f (FIG. 1B-2) embedded in the prosthetic stomach 30 along its length and communicating with the electronic circuit 50. The wires 55a and 55d are located in the outer tube 31 each between layers 31i and 31o and on opposing sides along the prosthetic stomach 30. Wires 55b and 55e are exposed between the inflation member pairs 36a-e and the outer tube 31 on opposing sides along the prosthetic bowel 30. Wires 55c and 55f are located in the inner tube 32 along the stomach 30 between layer 32i and 32o. Wire pairs 55a and 55d form an open circuit as do wire pairs 55b and 55e, and wire pairs 55c and 55f. The electronic circuit 50 is configured to sense a large drop in impedance in one or more of the pairs wires 55a-f, where a fluid closes the circuit of one or more of the wire pairs indicating potential leakage of fluid into, out of or within the stomach 30, e.g. from material external the prosthetic stomach 30, material within the inner member 32 of the stomach 30 or from an inflation member, or otherwise. In particular, a low impedance may be detected by the controller 51, which is configured to sense impedance changes in the wires 55a-f. The impedance of the pairs of wires 55a-f is periodically monitored by the controller 51. If a leak is detected a patient alarm may be triggered, e.g., by telemetrically delivering an alarm signal from the electronics unit 50 to an external device. Furthermore, the location or cause of the leak may be determined by which wires 55a-f have changed impedances. The wire pairs may be placed in different configurations within layers 31i, 31o, 32i, 32o or between the inner 32 and outer members 31, for example, they may be is parallel spiraled configurations to maximize the sensing of potential leaks.

The prosthetic stomach 30 also includes a conduit 56 through the prosthetic bowel 30, into a port 57 inside the inner member 32 for delivery a digestive enzyme, antibiotic material, or the like from a reservoir 58. The reservoir 58 is coupled to the controller 51 and may include a pump controlled by the controller 51 that provides a periodic or otherwise actuated (e.g. by a patient) injection of a material into the inner member 32. The reservoir 58 may also be implanted in soft tissue or may be included with the housing 180.

The prosthetic stomach 30 is illustrated in FIG. 1B in an inactive position in which a patient may ingest food and food may move from the fundus into the antrum portion 37 of the prosthetic stomach 30. In this position the pyloric valve 38 at the aborad end portion 34 is in a closed position with inflation member section 36g inflated. The inflation member sections 36a-f of the antrum portion 37 are relaxed and deflated.

FIGS. 1E-1J illustrate a sequence of mixing food and emptying the prosthetic stomach 30 of one embodiment of the invention. In FIG. 1E the valve 46a is opened and the pump 41 pumps inflation medium from the reservoir 49 into the inflation member section 36a through the conduit 39a. The inflation member section 36a is inflated to a predetermined pressure as sensed by pressure transducer 48 or alternatively as sensed by the motor. Once the inflation member section 36a is inflated, the valve 46a is closed by the valve actuating mechanism 60 (FIG. 1B). Inflation of the inflation member section 36a closes the orad end portion 33 of the prosthetic stomach 30 from the upper portion of the stomach 201. Material within the prosthetic stomach 30 is thus contained in the antrum portion 37.

Next, as shown in FIG. 1F, inflation member section 36b is inflated to grind material in the prosthetic stomach 30. The inflation member section 36b is inflated by opening the valve 46b and inflating by pumping fluid from the reservoir 49 into inflation member section 36b through conduit 39b. Thus, the materials remain in the antrum portion 37 without allowing them to move back in the direction of the inflation member pair 36a. The valve 46b is then closed. The inflation member section 36b may then be deflated and other inflation member sections 36c-36f may be inflated and deflated according to a predetermined sequence to mix material in the antrum portion 37. As shown in FIGS. 1E and 1F, the pyloric valve 38 is only slightly open, permitting fluids or small particles to pass through.

After some mixing has occurred, as illustrated in FIG. 1G, the pyloric valve 38 may be further relaxed by partially deflating inflation member section 36g. Thus as inflation members are inflated in an aborad direction, material that is sufficiently broken down may pass through the pyloric valve 38. In FIG.

1G, inflation member section 36b is inflated. The inflation member 36a has been deflated from a inflated position similar to that of FIG. 1F by selecting valve 46a, reversing the pump direction, pumping the inflation medium out of the inflation member section 36a back to the reservoir 49 and closing the valve 46a. As shown in FIG. 1H, inflation member section 36c is next inflated to advance material further through the prosthetic stomach 30. Before the adjacent inflation member section 36b is deflated, the inflation member section 36c is inflated by opening the valve 46c and by pumping fluid from the reservoir 49 into inflation member section 36c through conduit 39c. Thus, any materials are advanced further toward the pyloric valve 38. The valve 46c is then closed.

Referring to FIG. 1I, inflation member section 36b has been deflated by selecting the valve 46b, reversing the pump direction and pumping the inflation medium out of the inflation member pair 36b and closing the valve 46. The inflation member section 36d is inflated by selecting the valve 46d and pumping inflation medium into the inflation member section 36d. A number of inflation member sections may be provided in the prosthetic stomach 30 and the sequence of inflating and deflating the inflation members continues until the last inflation member sections 36e and 36f are inflated as illustrated in FIG. 1J.

If the materials have not been sufficiently broken down to pass through the pyloric valve 38 the mixing cycle may be repeated until they are sufficiently broken down.

FIGS. 4-6F illustrate a valve-actuating device 300 according to an embodiment of the invention. The valve-actuating device 300 comprises a cylinder 310 having a length Lc aligned parallel with the length Lh of the header 45 of the pump 41 and adjacent the valves 46a-g. The cylinder 310 includes a plurality of openings 320a-g, spaced a defined distance along the length Lc of the cylinder 310 with respect to the other openings so that each opening is aligned lengthwise with a corresponding one of the valves 46a-g. Each opening 320a-g is also spaced a defined discrete distance circumferentially from the other openings. The cylinder 310 is coupled to a stepper motor 330 that rotates the cylinder 310 according to instructions from the controller 51 (FIG. 1A) into discrete circumferential positions to interfacingly align a selected opening with a corresponding selected valve. Thus, the cylinder 310 may be rotated to discrete positions wherein in each position one of the openings 320a-g is interfacing a corresponding one of the valves 46a-g to be actuated.

A valve is actuated by a peg extending out of an interfacing opening in the cylinder 310 to engage and move the valve into an open position. Each opening 320a-g in the cylinder 310 includes concentrically moveable peg 321a-g respectively. Each of the pegs 321a-g is capable of being partially advanced in a circumferential direction out of the corresponding opening 320a-g in the cylinder 310. When interfacing with a corresponding valve 46a-g, a corresponding peg 321a-g may be advanced to engage and open the corresponding valve 46a-g to open it.

Once a valve is selected and the controller 51 instructs the stepper motor 330 to rotatably position the cylinder 310 accordingly, an actuating rod 323 is advanced through the cylinder 310 to engage and advance the corresponding aligned, interfacing peg out of the cylinder 310 to open the corresponding valve.

The actuating rod 323 slidably extends axially through an axial opening 313 in the cylinder 310. The rod 323 is coupled to a solenoid 328 that moves the rod 323 between two positions: a first resting position (FIG. 4-4A, FIGS. 6-6F) and a second valve actuating position (FIG. 5-5A). The solenoid 328 advances and retracts the rod 323 to and from a valve actuating position. The actuating rod 323 moves in a direction generally perpendicular to the circumferential sliding direction of the pegs 321a-g. The actuating rod 323 includes a central rod 324 and a plurality of staggered fins 325a-g having cammed surfaces 326a-g. In the first position, the fins 325a-g are staggered in a lengthwise relationship between the valves 46a-g and a second position, the fins 325a-g are generally aligned in a lengthwise relationship with the valves 46a-g. The cammed surfaces 326a-g are arranged so that when the rod 323 is advanced to the second position, a corresponding one of the cammed surfaces 326a-g will engage a corresponding one of the pegs 321a-g to move the corresponding one of the pegs 321a-g circumferentially out of a corresponding one of the openings 320a-g.

The axial opening 313 through the cylinder 310 includes a central rod portion 314 for receiving the rod 323 and a fin portion 315 for receiving in the fins 325a-g. The central rod portion 314 extends axially through the cylinder 310. The fin portion 315 of the axial opening 313 includes open portions 316a-g staggered in a lengthwise relationship between the valves 46a-g. Each open portion 316a-g is open within the rod opening 313 about the circumference of the cylinder 310 so that when the rod 323 is in the first position, the cylinder 310 is free to rotate without interference of the fins 325a-g. The fin portion 315 also includes a plurality of slits 317a-g circumferentially spaced from the other slits, wherein each slit extends longitudinally through the cylinder, between each of the open portions 316a-g and perpendicularly through a corresponding one of the openings 320a-g.

The fins 325a-g are aligned in a position with the circumferentially extending top portions facing the header 45. The cylinder 310 may be rotated when the rod 323 and fins 325a-g are in the first position. The cylinder when rotated to one of its discrete positions aligns a corresponding slit with the fins so that in the second position the fins advance through that slit. When the fins 325a-g are moved into the second position, the fins 325a-g extend through the slit corresponding to the opening that is positioned in alignment with a corresponding valve. In each discrete position the fins 325a-g are aligned with a slit permitting the corresponding fin to slide into the opening and engage the pin moving the pin out of the opening engaging the correspond valve with which it is aligned, thus actuating the corresponding valve. Each peg 321a-g is biased by a corresponding spring (329a only is shown) into a position circumferentially into the opening so that when the fins are retracted (e.g. FIG. 6), the pin moves back into the opening.

The controller 51 controls the timing and actuation of the cylinder 310 rotation and the solenoid 328 positioning. Referring to FIG. 4, the cylinder 310 is rotated to a position in which none of the pegs are aligned with valve 36a. The rod is in a first position in which the cylinder 310 may rotate freely. The cylinder 310 is then rotated as illustrated in FIG. 5 so that the opening 321a is aligned with the valve 46a. The rod 323 is advanced so that the fins 325a-g extend through the slit 317a. Fin 325a extends into the opening 320a that is aligned with the slit 325a and the cammed surface 326a of the fin 325a engages the peg 321a and advances it out of the opening 320a to actuate valve 46a. The valve 46a is opened and the pump 41 pumps fluid from the reservoir 49 into the inflatable member pair 36a. As illustrated in FIG. 6, the rod 323 is then retracted releasing the peg 321a, which is biased by spring 329a into the cylinder opening 320a, and the valve 46a is closed, leaving the inflation member pair 36a inflated.

Referring to FIGS. 2A-2C another embodiment of the invention is illustrated. A prosthesis includes a prosthetic pylorus 130 and a housing 180 containing a pump system similar to the pump system 40 described above with reference to FIGS. 1A-1J. The prosthetic pylorus 130 includes an outer support member 131, a series of inflatable member sections 136a-b and an inner member 132. The outer support member 131 comprises a flexible, relatively inelastic material such as, for example, polyethylene or polyurethane, and provides structural support for the pylorus (elastic materials may be used as well). The inner member 132 comprises a thin-walled, non-elastic flexible material such as polyethylene or polyurethane. The inner member 132 may be coated with an antibiotic surface, such as a silver coating, to reduce bacterial growth. The inner member 132 is attached to the outer support member 131 at the orad end portion 133 and the aborad end portion 134 of the prosthetic pylorus 130 (for example, by welding) to provide an isolated conduit through which material may pass. The orad end portion 133 and aborad end portion 134 of the outer support member 131 include relatively thicker portions for suturing the orad end portion 133 of the outer support member 131 to the stomach 100 and aborad end portion 134 of the outer support member 131 to the small intestine 101 as shown in FIG. 2A. The inner member 132 defines a conduit through which material pass from the stomach 100 into the small intestine 101. The inflatable member sections 136a-b are located between the outer support member 131 and the inner member 132 with the inner member 132 floating relatively loosely within the outer support member 131 so as to permit the inflatable member sections 136a-b to expand and contract.

The prosthesis 130 is implanted to replace the pylorus of the stomach. The inflatable member sections 136a-b and the inner member 132 form a valve 138. The inflatable members 136a-b are attached to the inside of the outer support member 131 between the outer support member 131 and the inner member 132 along the length of the prosthesis 130. According to this embodiment, the inflatable member section 136a forms an orad inflatable member pair and the inflatable member section 136b forms an aborad inflatable member pair. Each section of inflatable members converges together when inflated, to close the valve 138. The valve 138 is actuated by inflating sections 136a-b, which causes the inner member 132 to squeeze together to seal the conduit closed.

Each section 136a-b is coupled to and is fluid communication with a corresponding respective one of conduits 139a, 139b. Conduits 139a, 139b are used to selectively deliver inflation medium to and from sections 136a-b by an implanted pump system 140 (and valve actuator) and electronics unit 150 similar to the pump system 40 (and valve actuator 300) and electronics unit 50 described above with reference to FIGS. 1A-1J and FIGS. 4-6F.

Referring now to FIGS. 3A-3C, a supplemental pyloric valve 230 is illustrated implanted adjacent a pylorus 205 and in the duodenum 206. The supplemental pyloric valve 230 is coupled to an implanted housing 280 including a hermetically sealed pump 241 and controller 251 operating in a similar manner as pump system 40 (and valve actuator 300) and electronics unit 50 described above with reference to FIGS. 1A-J and FIGS. 4-6F The supplemental pylorus 230 includes an outer support member 231, a series of inflatable members sections 236a-b and an inner member 232. The outer support member 231 comprises a flexible, relatively inelastic material such as, for example, polyethylene or polyurethane, and provides structural support for the pylorus (elastic materials may be used as well). The inner member 232 comprises a thin-walled, non-elastic flexible material such as polyethylene or polyurethane. The inner member 232 may be coated with an antibiotic surface, such as a silver coating, to reduce bacterial growth. The inner member 232 is attached to the outer support member 231 at the orad end portion 233 and the aborad end portion 234 of the supplemental pyloric valve 230 (for example, by welding) to provide an isolated conduit through which material may pass. The orad end portion 233 of the support member 231 is sutured on to the inner wall 207 of the duodenum adjacent the pylorus 205. The aborad end portion 234 of the outer support member 231 is sutured to duodenum 206 downstream of the orad end portion as shown in FIG. 3A. The inner member 232 defines a conduit through which material pass from the pylorus 205 into the small intestine 206. The inflatable member sections 236a-b are located between the outer support member 231 and the inner member 232 with the inner member 232 floating relatively loosely within the outer support member 231 so as to permit the inflatable member sections 236a-b to expand and contract.

The supplemental pyloric valve 230 is implanted to supplement the pylorus of the stomach by further controlling the exit of material from the stomach through the pylorus and into the duodenum. In one embodiment this is done to retain food in the stomach for a greater duration to treat obesity and/or dumping syndrome. The inflatable member sections 236a-b and the inner member 232 form a valve 238. The inflatable members 236a-b are attached to the inside of the outer support member 231 between the outer support member 231 and the inner member 232 along the length of the prosthesis 230. According to this embodiment, the inflatable member section 236a forms an orad inflatable member pair and the inflatable member section 236b forms an aborad inflatable member pair. Each pair of inflatable members converges together when inflated, to close the valve 238. The valve 238 is actuated by inflating sections 236a-b, which causes the inner member 232 to squeeze together to seal the conduit closed.

Each section 236a-b is coupled to and is fluid communication with a corresponding respective one of conduits 239a, 239b. Conduits 239a, 239b extend out of the duodenum and are coupled to the pump 241. Conduits 239a, 239b are used to selectively deliver inflation medium to and from sections 236a-b by an implanted pump and control controller similar to the pump system 40 and electronics unit 50 described above with reference to FIGS. 1A-1J and FIGS. 4-6F.

While the invention has been described with reference to particular embodiments, it will be understood to one skilled in the art that variations and modifications may be made in form and detail without departing from the spirit and scope of the invention.

For example, the invention may be practiced replacing or augmenting all or part of a portion of the digestive tract such as the bowel or small intestine as described, for example in U.S. application entitled "IMPLANTABLE DIGESTIVE TRACT ORGAN" filed on even date herewith, incorporated herein by reference.

What is claimed is:

1. An implantable prosthetic digestive organ comprising:
   an elongate body having an orad end, a aborad end and a lumen therethrough, the elongate body configured for implantation such that the orad end is attached to a portion of a patient's digestive tract from which digestive material is passed into the lumen and the aborad end is positioned to allow removal of the digestive material from the lumen;
   at least two inflatable members disposed along the body which are capable of extending into the lumen upon inflation and retracting from the lumen upon deflation; and
   a pump connected with the inflatable members which causes the inflation and deflation due to actuation by a controller; and wherein the at least two inflatable members are capable of being inflated and deflated in a sequence which causes churning the digestive material within the lumen so as to expedite breaking down of the digestive material.

2. An implantable prosthetic digestive organ comprising:
an elongate body having an orad end, a aborad end and a lumen therethrough, the elongate body configured for implantation such that the orad end is attached to a portion of a patient's digestive tract from which digestive material is passed into the lumen and the aborad end is positioned to allow removal of the digestive material from the lumen;
at least two inflatable members disposed along the body which are capable of extending into the lumen upon inflation and retracting from the lumen upon deflation; and
a pump connected with the inflatable members which causes the inflation and deflation due to actuation by a controller; and
wherein the at least two inflatable members are capable of occluding the lumen upon inflation so as to prevent significant passage of digestive material therethrough, wherein the at least two inflatable members include a plurality of inflatable members disposed along the elongate body, wherein some of the inflatable members are capable of occluding the lumen while others of the inflatable members churn the digestive material.

3. An implantable prosthetic digestive organ comprising:
an elongate body having an orad end, an aborad end and a lumen therethrough, the elongate body configured for implantation such that the orad end is attached to a portion of a patient's digestive tract from which digestive material is passed into the lumen and the aborad end is positioned to allow removal of the digestive material from the lumen;
at least two inflatable members disposed along the body which are capable of extending into the lumen upon inflation and retracting from the lumen upon deflation; and
a pump connected with the inflatable members which causes the inflation and deflation due to actuation by a controller; and
wherein the at least two inflatable members are capable of occluding the lumen upon inflation so as to prevent significant passage of digestive material therethrough when operating under a first mode and churn the digestive material when operating under a second mode.

* * * * *